United States Patent
Lim et al.

(10) Patent No.: US 11,377,505 B2
(45) Date of Patent: Jul. 5, 2022

(54) METHODS AND FORMULATIONS FOR REDUCING RECONSTITUTION TIME OF LYOPHILIZED POLYPEPTIDES

(71) Applicant: Genentech, Inc., South San Francisco, CA (US)

(72) Inventors: Fredric John Lim, South San Francisco, CA (US); Jacob Edward Luoma, South San Francisco, CA (US); Isidro Angelo Eleazar Zarraga, Millbrae, CA (US); Christopher Michael Heynes, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 35 days.

(21) Appl. No.: 16/420,974

(22) Filed: May 23, 2019

(65) Prior Publication Data

US 2019/0389974 A1    Dec. 26, 2019

Related U.S. Application Data

(63) Continuation of application No. PCT/US2017/068024, filed on Dec. 21, 2017.

(60) Provisional application No. 62/438,232, filed on Dec. 22, 2016.

(51) Int. Cl.
| | |
|---|---|
| *A61K 39/395* | (2006.01) |
| *C07K 17/10* | (2006.01) |
| *A61K 9/19* | (2006.01) |
| *C07K 1/02* | (2006.01) |
| *C07K 16/06* | (2006.01) |

(52) U.S. Cl.
CPC ............... *C07K 17/10* (2013.01); *A61K 9/19* (2013.01); *C07K 1/02* (2013.01); *C07K 16/065* (2013.01); *C07K 2317/50* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,515,893 A | 5/1985 | Kung et al. | |
| 5,091,178 A | 2/1992 | Hellstrom et al. | |
| 5,091,313 A | 2/1992 | Chang | |
| 5,622,700 A | 4/1997 | Jardieu et al. | |
| 5,693,762 A | 12/1997 | Queen et al. | |
| 5,714,338 A | 2/1998 | Wai Fei et al. | |
| 6,171,586 B1 | 1/2001 | Lam | |
| 6,267,958 B1 | 7/2001 | Andya | |
| 8,071,097 B2 | 12/2011 | Wu | |
| 2004/0191244 A1 | 9/2004 | Presta | |
| 2005/0260186 A1 | 11/2005 | Bookbinder et al. | |
| 2006/0104968 A1 | 5/2006 | Bookbinder et al. | |
| 2014/0044717 A1 | 2/2014 | Kranz | |

FOREIGN PATENT DOCUMENTS

| | | |
|---|---|---|
| WO | WO199304173 A1 | 3/1993 |
| WO | WO199519181 A1 | 7/1995 |
| WO | WO199523865 A1 | 9/1995 |
| WO | WO199640210 A1 | 12/1996 |
| WO | WO199726912 A2 | 7/1997 |
| WO | WO199726912 A3 | 10/1997 |
| WO | WO199806248 A2 | 2/1998 |
| WO | WO199806248 A3 | 5/1998 |
| WO | WO199823761 A1 | 6/1998 |
| WO | WO199851793 A1 | 11/1998 |
| WO | WO199901556 A2 | 1/1999 |
| WO | WO199901556 A3 | 4/1999 |
| WO | WO200075348 A1 | 12/2000 |
| WO | WO200140309 A2 | 6/2001 |
| WO | WO200140309 A3 | 11/2001 |
| WO | WO2003070760 A2 | 8/2003 |
| WO | WO2003070760 A3 | 3/2004 |
| WO | WO2004070011 A2 | 8/2004 |
| WO | WO2004070011 A3 | 11/2005 |
| WO | WO2006044908 A2 | 4/2006 |
| WO | WO2006044908 A3 | 8/2006 |
| WO | WO2008011348 A2 | 1/2008 |
| WO | WO2008011348 A3 | 7/2008 |
| WO | WO2012109429 A2 | 8/2012 |
| WO | WO2012109429 A3 | 10/2012 |
| WO | WO2014078268 A2 | 5/2014 |
| WO | WO2014078268 A3 | 11/2014 |
| WO | WO2015107214 A1 | 7/2015 |

OTHER PUBLICATIONS

Munjal et al., Journal of Pharmaceutical Sciences, vol. 104, pp. 87-97, 2015.*
Andya, J.D. et al. (Apr. 4, 2003). "Mechanisms of Aggregate Formation and Carbohydrate Excipient Stabilization of Lyophilized Humanized Monoclonal Antibody Formulations," 5(2):Article 10, 1-11 pages.
Bogdani, E. et al. (2013, e-pub. Feb. 28, 2013). "Optimization of Freeze-Drying Cycle for Tert-Butanol-Based Formulations of Ibuprofen," Drying Technology 31:308-313.
Ceriani, R.L. et al. (Dec. 1, 1995). "Biological Activity of Two Humanized Antibodies Against Two Different Breast Cancer Antigens and Comparison to Their Original Murine Forms," Cancer Res. 55(23):5852s-5856s.
Choy, E.H.S. et al. (Jan. 1996). "Percentage of Anti-CD4 Monoclonal Antibody-Coated Lymphocytes in the Rheumatoid Joint is Associated With Clinical Improvement," Arthritis Rheum 39(1):52-56.
Cleland, J.L. et al. "A Specific Molar Ratio of Stabilizer to Protein is Required for Storage Stability of a Lyophilized Monoclonal Antibody," J. of Pharmaceutical Sciences 90(3):310-321, (Mar. 2001).

(Continued)

Primary Examiner — Yunsoo Kim
(74) Attorney, Agent, or Firm — Morrison & Foerster LLP

(57) ABSTRACT

The present invention relates to methods and formulations useful for reducing the reconstitution time of lyophilized polypeptides.

17 Claims, 10 Drawing Sheets

(56) References Cited

OTHER PUBLICATIONS

Dhainaut, J.-F. A. et al. (1995). "CDP571, A humanized Antibody to Human Tumor Necrosis Factor-α: Safety, Pharmacokinetics, Immune Response, and Influence of the Antibody on Cytokine Concentrations in Patients With Septic Shock," Crit. Care Med. 23(9):1461-1469.
Ellis, J.H. et al. (1995). "Engineered Anti-CD38 Monoclonal Antibodies for Immunotherapy of Multiple Myeloma," J. Immunol. 155(2):925-937.
Flatman, S. et al. (2007, e-pub. Dec. 11, 2006). "Process analytics for Purification of Monoclonal Antibodies," J. Chromatogr. B. 848:79-87.
Graziano, R.F. et al. (1995). "Construction and Characterization of a Humanized Anti-γ-Ig Receptor Type I (FcγRI) Monoclonal Antibody," J. Immunol. 155(10):4996-5002.
Hourmant, M. et al. (Aug. 1994). "Administration of an Anti-CD11a Monoclonal Antibody in Recipients of Kidney Transplantation: A Pilot Study," Transplantation 58:377-380.
International Preliminary Report on Patentability, dated Jun. 25, 2019, for PCT Application No. PCT/US2017/068024, filed Dec. 21, 2017, 9 pages.
International Search Report and Written Opinion, dated May 7, 2018, for PCT Application No. PCT/US2017/068024, filed Dec. 21, 2017, 16 pages.
Jones, A.J.S. (1993). Analysis of Polypeptides and Proteins, Adv. Drug Delivery Rev. 10:29-90.
Jurcic, J.G. et al. (Dec. 1, 1995). "Radiolabeled Anti-CD33 Monoclonal Antibody M195 for Myeloid Leukemias," Cancer Res. 55(23 Suppl):5908s-5910s.
Juweid, M. et al. (Dec. 1, 1995). "Treatment of Non-Hodgkin's Lymphoma with Radiolabeled Murine, Chimeric, or Humanized LL2, and Anti-CD22 Monoclonal Antibody," Cancer Res 55(23 Suppl):5899s-5907s.
Litton, M.J. et al. (1996). "Antibody-Targeted Superantigen Therapy Induces Tumor-Infiltrating Lymphocytes, Excessive Cytokine Production, and Apoptosis in Human Colon Carcinoma," Eur J. Immunol. 26(1):1-9.
Lorenz, H.-M. et al. (1996). "In Vivo Blockade of TNF-α by Intravenous Infusion of a Chimeric Monoclonal TNF-α Antibody in Patients With Rheumatoid Arthritis: Short Term Cellular and Molecular Effects," J. Immunol. 156(4):1646-1653.
Muranyi, A. et al. "Development of Gel-Forming Lyophilized Formulation With Recombinant Human Thrombin," Drug Development and Industrial Pharmacy 41(9):1566-1573, (2015).
Presta, L.G. et al. (Sep. 1, 1993). "Humanization of an Antibody Directed Against IgE," J. Immunol. 151(5):2623-2632.
Richman, C.M. et al. (Dec. 1, 1995). "Radioimmunotherapy for Breast Cancer Using Escalating Fractionated Doses of 131I-Labeled Chimeric L6 Antibody with Peripheral Blood Progenitor Cell Transfusions," Cancer Res. 55(23Supp):5916s-5920s.
Riechmann, L. et al. (Mar. 24, 1988). "Reshaping Human Antibodies for Therapy," Nature 332:323-329.
Sharkey, R.M. et al. (Dec. 1, 1995). "Evaluation of a Complementarity-Determining Region-Grafted (Humanized) Anti-Carcinoembryonic Antigen Monoclonal Antibody in Preclinical and Clinical Studies," Cancer Res. 55(23Suppl):5935s-5945s.
St John, R.C. et al. (Mar. 1993). "Immunologic Therapy for ARDS, Septic Shock, and Multiple-Organ Failure," Chest 103(3):932-943.
Stoppa, A.M. et al. (Apr. 1991). "Anti-LFA1 Monoclonal Antibody (25.3) for Treatment of Steroid-Resistant Grade III-IV Acute Graft-Versus-Host Disease," Transplant Intl. 4(1):3-7.
Teagarden, D.L. et al. (Mar. 2002). "Practical Aspects of Lyophilization Using Non-Aqueous Co-Solvent Systems," Eur J Pharma Sci 15(2):115-133.
Vessot, S. et al. (2012, e-pub. Jan. 30, 2012). "A Review on Freeze Drying of Drugs with tert-Butanol (TBA) + Water Systems: Characteristics, Advantages, Drawbacks," 30(4):377-385.
Wittaya-Areekul, S. et al. (2002). "Freeze-Drying of tert-Butanol/Water Cosolvent Systems: A Case Report on Formation of a Friable Freeze-Dried Powder of Tobramycin Sulfate," 91:1147-1155.
Zhang, Y. et al. (Apr. 17, 2009, e-pub. Dec. 24, 2009). "Conformational and Bioactivity Analysis of Insulin: Freeze-Drying TBA/Water Co-Solvent System in the Presence of Surfactant and Sugar," Int J Pharmaceutics 371(1-2):71-81.
Bhambhani, A. et al. (Jan. 1, 2010). "Lyophilization Strategies for Development of a High-Concentration Monoclonal Antibody Formulation: Benefits and Pitfalls," American Pharmaceutical Review, retrieved from the Internet URL:http://www.americanpharmaceuticalreview.com/FeaturedArticles/117600-Lyophilization-Strategies-for-Development-of-a . . . , last visited May 11, 2015, 9 pages.
Jorgensen, L. et al. (2009, e-pub. Aug. 13, 2009). "Recent Trends in Stabilising Peptides and Proteins in Pharmaceutical Formulation—Considerations in the Choice of Excipients," Expert Opinion on Drug Delivery 6(11):1219-1230.
Schwegman, J.J. et al. (Jan. 1, 2005). "Practical Formulation and Process Development of Freeze-Dried Products," Pharmaceutical Development and Technology 10(2):151-173.
Teagarden, D.L. et al. (Nov. 30, 2009). "Chapter 10: Practical Aspects of Freeze-Drying of Pharmaceutical and Biological Products Using Nonaqueous Cosolvent Systems," Freeze Drying/Lyophilization of Pharmaceutical and Biological Products, pp. 254-287.
Wang, W. (1999). "Instability, Stabilization, and Formulation of Liquid Protein Pharmaceuticals," International Journal of Pharmaceutics 185:129-188.
Wang, W. et al. "Antibody Structure, Instability, and Formulation," J. of Pharmaceutical Sciences 96(1):1-26 (Jan. 2007).
Warne, N.W. et al. (2011, e-pub. Mar. 13, 2011). "Development of High Concentraction Protein Biopharmaceuticals: The Use of Platform Approaches in Formulation Development," European Journal of Pharmaceutics and Biopharmaceutics 78:208-212.
Yong, Z. et al. (Apr. 17, 2009, e-pub. Dec. 24, 2008). "Conformational and bioactivity analysis of insulin: Freeze-drying TBA/water co-solvent system in the presence of surfactant and sugar," International Journal of Pharmaceutics 371(1-2):71-81.
Cao, W. et al. (Oct. 2013, e-pub. May 20, 2013). "Rational Design of Lyophilized High Concentration Protein Formulations—Mitigating the Challenge of Slow Reconstitution With Multidisciplinary Strategies," European Journal of Pharmaceutics and Biopharmaceutics 85(2):287-293.

* cited by examiner

METHODS AND FORMULATIONS FOR REDUCING RECONSTITUTION TIME OF LYOPHILIZED POLYPEPTIDES

CROSS-REFERENCE TO RELATED APPLICATIONS

This application is a continuation of International Patent Application No. PCT/US2017/068024, filed Dec. 21, 2017, which claims priority to and the benefit of U.S. Provisional Application No. 62/438,232, filed Dec. 22, 2016, each of which is hereby incorporated by reference in its entirety.

FIELD OF THE INVENTION

The present invention relates to methods and formulations useful for reducing the reconstitution time of lyophilized polypeptides.

BACKGROUND OF THE INVENTION

Biological molecules for pharmaceutical or other uses are often lyophilized, a process in which water is removed from a liquid composition after it is frozen and placed under vacuum. In general, lyophilization improves stability of a polypeptide composition by the removal of water (as many biologic chemical degradations are hydrolytic) and by decreasing the overall mobility of the system (as dynamic movement of sidechains and molecules is necessary for chemical and physical degradation events to occur). Lyophilized polypeptides are subsequently reconstituted prior to use, often in the very same containers or vials in which they were lyophilized and stored. Short reconstitution time is preferable, especially in the context of reconstitution of a lyophilized medicinal polypeptide composition (e.g., an antibody composition).

High-concentration and high-dose (e.g., gram quantities) of lyophilized pharmaceutical products pose unique processing and handling challenges, including long lyophilization cycles and often long reconstitution times. (See, e.g., American Pharmaceutical Review, 13 (2010), pp. 31-32 34-38.) One approach to controlling reconstitution time for biological molecules is to decrease the protein concentration, thereby increasing the fill volume. However, this approach can be unsuitable for high-dose formulations where increasing fill volume would necessitate the use of multiple vials per dose. In such cases, alternative lyophilization formulations and methods are required.

The presence of tert-butyl alcohol (TBA) in lyophilization formulations has been shown to improve reconstitution time of small quantities or low-doses (e.g., milligram quantities) of biological molecules (See, e.g., U.S. Patent Application Publication No. US 2014/0044717; Nail et al., (2002) J Pharma Sci. Vol. 91; Degobert et al., (2016) Drying Technology; Yong et al., (2009) Int J Pharmaceutics, 371:71-81; Teagarden and Baker (2002) Eur J Pharma Sci 15:115-133; Vessot and Andrieu (2012) Drying Technology (2012) 30:377-385).

However, the use of TBA in a co-solvent system in lyophilized formulations of biological molecules and its effects on reconstitution time and polypeptide stability has not been well-characterized in polypeptide formulations containing large quantities of protein (e.g., gram quantities) or with high protein concentrations.

Thus a need exists for methods and formulations of lyophilized biological molecules for large quantities and concentrations (i.e., high-concentration, high-dose) polypeptide compositions, including antibody compositions, which provide reduced or fast reconstitution times as well as maintain integrity and stability of the biological molecule. The present invention meets this need by providing methods and formulations for reducing reconstitution times of lyophilized polypeptides, in which the methods and formulations maintain integrity and stability of the lyophilized polypeptides, in particular for lyophilized antibody compositions of high-concentration and/or high-dose formulations.

SUMMARY OF THE INVENTION

The present invention provides methods and formulations useful for reducing the reconstitution time of lyophilized polypeptides, for example, lyophilized antibody compositions.

In one embodiment, the present invention provides a method for reducing the reconstitution time of a lyophilized polypeptide composition, wherein the method comprises preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent, wherein the time for reconstituting the polypeptide lyophilized in the presence of TBA is less than the time for reconstituting the same amount of the same polypeptide lyophilized in the absence of TBA. In some embodiments, the amount of TBA added to the liquid polypeptide composition to form a liquid polypeptide/TBA mixture is between about 0.5% to about 20% by volume. In other embodiments, the amount of TBA added to the liquid polypeptide composition to form the liquid polypeptide/TBA mixture is selected from the group consisting of 0.5%, 1%, 2.5%, 5%, 7.5%, 10%, 12.5%, 15%, 17.5%, and 20% by volume. In yet other embodiments, the amount of TBA added to the liquid polypeptide composition to form the liquid polypeptide/TBA mixture is between about 1% to about 20% by volume, about 1% to about 10% by volume, about 1% to about 5% by volume, about 5% to about 20% by volume, or about 5% to about 10% by volume. In one embodiment, the TBA is added to the liquid composition comprising the polypeptide immediately prior to freezing the liquid polypeptide/TBA mixture. In certain embodiments, the polypeptide is an antibody. In some embodiments, the polypeptide is an antibody and the method comprises preparing a liquid composition comprising the antibody and a sugar at a molar ratio of sugar:antibody of at least about 360:1 prior to adding TBA to the liquid composition.

In one embodiment, the present invention provides a method for reducing the reconstitution time of a lyophilized antibody composition, wherein the method comprises preparing a liquid composition comprising the antibody, adding tert-butyl alcohol (TBA) to the liquid composition to form a liquid antibody/TBA mixture, freezing the liquid antibody/TBA mixture, lyophilizing the liquid antibody/TBA mixture to form a lyophilized antibody composition, and reconstituting the lyophilized antibody composition with a diluent, wherein the time for reconstituting the antibody lyophilized in the presence of TBA is less than the time for reconstituting the same amount of the same antibody lyophilized in the absence of TBA. In some embodiments, the amount of TBA added to the liquid polypeptide composition to form a liquid polypeptide/TBA mixture is between about 0.5% to about 20% by volume. In other embodiments, the amount of TBA added to the liquid polypeptide composition to form the liquid polypeptide/TBA mixture is selected from the group consisting of 0.5%, 1%, 2.5%, 5%, 7.5%, 10%, 12.5%, 15%, 17.5%, and 20% by volume. In yet other embodiments, the amount of TBA added to the liquid polypeptide composition to form the liquid polypeptide/TBA mixture is between about 1% to about 20% by volume, about 1% to about 10% by volume, about 1% to about 5% by volume, about 5% to about 20% by volume, or about 5% to about 10% by volume. In some embodiments, the method comprises preparing a liquid composition comprising the antibody and a sugar at a molar ratio of sugar:antibody of at least about 360:1 prior to adding TBA to the liquid composition. In one embodiment, the TBA is added to the liquid composition comprising the polypeptide immediately prior to freezing the liquid polypeptide/TBA mixture. In one embodiment, the antibody is a monoclonal antibody. In one embodiment, the antibody is a human monoclonal antibody. In one embodiment, the antibody is a humanized monoclonal antibody. In one embodiment, the antibody is a chimeric antibody. In one embodiment, the antibody is an antibody fragment. In one embodiment, the antibody is a bispecific antibody. In one embodiment, the antibody is an antibody-drug conjugate (e.g., an immunoconjugate).

In one embodiment, the present invention provides a method for reducing the reconstitution time of a lyophilized polypeptide composition, wherein the method comprises preparing a liquid composition comprising the polypeptide, wherein the concentration of the polypeptide in the liquid composition comprising the polypeptide is between about 10 mg/ml to about 150 mg/ml, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent, wherein the time for reconstituting the polypeptide lyophilized in the presence of TBA is less than the time for reconstituting the same amount of the same polypeptide lyophilized in the absence of TBA. In some embodiments, the concentration of the polypeptide in the liquid composition comprising the polypeptide is between about 10 mg/ml to about 250 mg/ml, between about 25 mg/ml to about 250 mg/ml, between about 50 mg/ml to about 250 mg/ml, between about 100 mg/ml to about 250 mg/ml, between about 150 mg/mml to about 250 mg/ml, between about 25 mg/ml to about 100 mg/ml, between about 50 mg/ml to about 100 mg/ml, between about 25 mg/ml to about 125 mg/ml, or between about 50 mg/ml to about 125 mg/ml. In some embodiments, the concentration of the polypeptide in the liquid composition comprising the polypeptide is about 25 mg/ml, about 40 mg/ml, about 50 mg/ml, about 60 mg/ml, about 70 mg/ml, about 100 mg/ml, about 125 mg/ml, about 150 mg/ml, about 200 mg/ml, or about 250 mg/ml. In certain embodiments, the polypeptide is an antibody. In some embodiments, the amount of TBA added to the liquid polypeptide composition to form a liquid polypeptide/TBA mixture is between about 0.5% to about 20% by volume. In some embodiments, the polypeptide is an antibody and the method comprises preparing a liquid composition comprising the antibody and a sugar at a molar ratio of sugar:antibody of at least about 360:1 prior to adding TBA to the liquid composition.

In one embodiment, the present invention provides a method for reducing the reconstitution time of a lyophilized polypeptide composition, wherein the method comprises preparing a liquid composition comprising the polypeptide, wherein the amount of the polypeptide in the liquid composition comprising the polypeptide is between about 150 mg to about 11 grams, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent, wherein the time for reconstituting the polypeptide lyophilized in the presence of TBA is less than the time for reconstituting the same amount of the same polypeptide lyophilized in the absence of TBA. In some embodiments, the amount of the polypeptide in the liquid composition comprising the polypeptide is about 150 mg, about 250 mg, about 500 mg, about 750 mg, about 1 gram, about 2 grams, about 3 grams, about 4 grams, about 5 grams, about 6 grams, about 7 grams, about 8 grams, about 9 grams, about 10 grams, or about 11 grams. In some embodiments, the amount of the polypeptide in the liquid composition comprising the polypeptide is between about 150 mg to 11 grams. In some embodiments, the amount of the polypeptide in the liquid composition comprising the polypeptide is between about 150 mg to about 1 gram, between about 500 mg to about 1 gram, between about 500 mg to about 5 grams, between about 1 gram to about 5 grams, between about 1 gram to about 10 grams, or between about 5 grams to about 10 grams. In some embodiments, the quantity of the polypeptide in the liquid composition comprising the polypeptide is greater than 11 grams. In certain embodiments, the polypeptide is an antibody. In some embodiments, the amount of TBA added to the liquid polypeptide composition to form a liquid polypeptide/TBA mixture is between about 0.5% to about 20% by volume. In some embodiments, the polypeptide is an antibody and the method comprises preparing a liquid composition comprising the antibody and a sugar at a molar ratio of sugar:antibody of at least about 360:1 prior to adding TBA to the liquid composition.

In one embodiment, the present invention provides a method for reducing the reconstitution time of a lyophilized polypeptide composition, wherein the method comprises preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent, wherein the time for reconstituting the polypeptide lyophilized in the presence of TBA is less than the time for reconstituting the same amount of the same polypeptide lyophilized in the absence of TBA, wherein the time for reconstituting the lyophilized polypeptide composition which was lyophilized in the presence of TBA is reduced by about 40% to about 95% compared to the time for reconstituting the same amount of the same polypeptide composition lyophilized in the absence of TBA. In some embodiments, the time for reconstituting the lyophilized polypeptide composition which was lyophilized in the presence of TBA is reduced by about 50%, about 60%, about 70%, about 80%, about 90%, about 95%, about 50% to about 60%, about 60% to about 70%, about 70% to about 80%, about 80% to about 90%, or about 90% to about 95% compared to the time for reconstituting the same amount of the same polypeptide composition lyophilized in the absence of TBA. In some embodiments, the polypeptide is an antibody and the method comprises preparing a liquid composition comprising the antibody and a sugar at a molar ratio of sugar:antibody of at least about 360:1 prior to adding TBA to the liquid composition.

In some embodiments of the present invention, the liquid polypeptide/TBA mixture is lyophilized in a vial, a syringe (including dual-chamber syringe), or a cartridge. In some embodiments, the liquid polypeptide/TBA mixture is lyophilized in a glass vial. In some embodiments, the vial is a 6 cc vial, a 10 cc vial, a 15 cc vial, a 20 cc vial, a 50 cc vial, or a 100 cc vial. In some embodiments, the glass vial is a 6 cc vial, a 10 cc vial, a 15 cc vial, a 20 cc vial, a 50 cc vial, or a 100 cc vial. In some embodiments, the vials have a capacity or fill volume of 0.1 ml, 0.3 ml, 0.5 ml, 1 ml, 2 ml, 2.5 ml, 5 ml, 10 ml, 20 ml, 25 ml, 50 ml, or 100 ml. In some embodiments, the glass vials have a capacity or fill volume of 0.1 ml, 0.3 ml, 0.5 ml, 1 ml, 2 ml, 2.5 ml, 5 ml, 10 ml, 20 ml, 25 ml, 50 ml, or 100 ml.

In some embodiments, reconstituting the lyophilized polypeptide composition is performed under conditions in which reconstituting the lyophilized polypeptide composition is performed under a vacuum. In some embodiment, the present invention provides a method for reducing the reconstitution time of a lyophilized polypeptide composition, wherein the method comprises preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent, wherein the reconstituting the lyophilized polypeptide composition is performed under conditions in which the lyophilized polypeptide composition is under a vacuum, and further wherein the time for reconstituting the polypeptide lyophilized in the presence of TBA is less than the time for reconstituting the same amount of the same polypeptide lyophilized in the absence of TBA. In some embodiments, the vacuum is a deep vacuum. In some embodiments, the vacuum is a partial vacuum. In certain embodiments, the vacuum is less than 100 Torr. In certain embodiments, the vacuum is less than 50 Torr. In certain embodiments, the vacuum is between 100 mTorr and 50 Torr. In one embodiment, the vacuum is at 100 mTorr. In some embodiments, the polypeptide is an antibody and the method comprises preparing a liquid composition comprising the antibody and a sugar at a molar ratio of sugar:antibody of at least about 360:1 prior to adding TBA to the liquid composition.

In some embodiments, reconstituting the lyophilized polypeptide composition is performed using a shaker, such as a mechanical shaker. In one embodiment, the present invention provides a method for reducing the reconstitution time of a lyophilized polypeptide composition, wherein the method comprises preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent by using a shaker, wherein the time for reconstituting the polypeptide lyophilized in the presence of TBA is less than the time for reconstituting the same amount of the same polypeptide lyophilized in the absence of TBA. In some embodiments, the vial or container is placed on the shaker. In some embodiments, the polypeptide is an antibody and the method comprises preparing a liquid composition comprising the antibody and a sugar at a molar ratio of sugar:antibody of at least about 360:1 prior to adding TBA to the liquid composition.

In some embodiments, reconstituting the lyophilized polypeptide composition is performed under conditions in which the lyophilized polypeptide composition is under a vacuum and using a shaker. In one embodiment, the present invention provides a method for reducing the reconstitution time of a lyophilized polypeptide composition, wherein the method comprises preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, and reconstituting the lyophilized polypeptide composition with a diluent by using a shaker, wherein the reconstituting the lyophilized polypeptide composition is performed under conditions in which the lyophilized polypeptide composition is under a vacuum, and further wherein the time for reconstituting the polypeptide lyophilized in the presence of TBA is less than the time for reconstituting the same amount of the same polypeptide lyophilized in the absence of TBA. In some embodiments, the vacuum is a deep vacuum. In some embodiments, the vacuum is a partial vacuum. In certain embodiments, the vacuum is less than 100 Torr. In certain embodiments, the vacuum is less than 50 Torr. In certain embodiments, the vacuum is between 100 mTorr and 50 Torr. In one embodiment, the vacuum is at 100 mTorr. In some embodiments, the polypeptide is an antibody and the method comprises preparing a liquid composition comprising the antibody and a sugar at a molar ratio of sugar:antibody of at least about 360:1 prior to adding TBA to the liquid composition.

The present invention provides liquid polypeptide formulations suitable for lyophilization. In some embodiments, the present invention provides liquid polypeptide formulations suitable for lyophilization, wherein the formulation comprises the polypeptide, a diluent, and TBA, wherein the time for reconstituting the polypeptide lyophilized in the presence of TBA is less than the time for reconstituting the same amount of the same polypeptide lyophilized in the absence of TBA. In some embodiments, the amount of TBA in the liquid formulation is between about 0.5-20% by volume. In some embodiments, the amount of TBA in the liquid formulation is selected from the group consisting of 0.5%, 1%, 2.5%, 5%, 7.5%, 10%, 12.5%, 15%, 17.5%, and 20% by volume. In other embodiments, the amount of TBA added to the liquid polypeptide composition to form the liquid polypeptide/TBA mixture is between about 1% to about 20% by volume, between about 1% to about 10% by volume, between about 1% to about 5% by volume, between about 5% to about 20% by volume, or between about 5% to about 10% by volume. In one embodiment, the TBA is added to the liquid composition comprising the polypeptide immediately prior to freezing the liquid polypeptide/TBA mixture. In certain embodiments, the polypeptide is an antibody. In some embodiments, the polypeptide is an antibody and the formulation further comprises a sugar at a molar ratio of sugar:antibody of at least about 360:1.

The present invention provides a lyophilized polypeptide composition, wherein the lyophilized polypeptide composition is produced by preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, wherein upon reconstitution of the lyophilized polypeptide composition with a diluent, the time for reconstituting the polypeptide lyophilized in the presence of TBA is less than the time for reconstituting the same amount of the same polypeptide lyophilized in the absence of TBA. In some embodiments, the amount of TBA in the liquid formulation is between about 0.5% to about 20% by volume. In some embodiments, the amount of TBA in the liquid formulation is selected from the group consisting of 0.5%, 1%, 2.5%, 5%, 7.5%, 10%, 12.5%, 15%, 17.5%, and 20% by volume. In other embodiments, the amount of TBA added to the liquid polypeptide composition to form the liquid polypeptide/TBA mixture is between about 1% to about 20% by volume, between about 1% to about 10% by volume, between about 1% to about 5% by volume, between about 5% to about 20% by volume, or between about 5% to about 10% by volume. In one embodiment, the TBA is added to the liquid composition comprising the polypeptide immediately prior to freezing the liquid polypeptide/TBA mixture. In certain embodiments, the polypeptide is an antibody. In certain embodiments, the addition of TBA to the polypeptide formulation has no effect on the integrity or stability of the polypeptide. In some embodiments, the polypeptide is an antibody and the lyophilized polypeptide composition is produced by preparing a liquid composition comprising the antibody and a sugar at a molar ratio of sugar:antibody of at least about 360:1 prior to adding TBA to the liquid composition.

In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent, wherein the time for reconstituting the antibody lyophilized in the presence of TBA is less than the time for reconstituting the same amount of the same antibody lyophilized in the absence of TBA. In some embodiments, the amount of TBA added to the liquid antibody composition to form the liquid antibody/TBA mixture is selected from the group consisting of 5%, 7.5%, 10%, 12.5%, 15%, 17.5%, and 20% by volume. In some embodiments, the amount of TBA added to the liquid antibody composition to form the liquid antibody/TBA mixture is about 5%-6% by volume. In yet other embodiments, the amount of TBA added to the liquid antibody composition to form the liquid antibody/TBA mixture is between about 5% to about 10% by volume. In one embodiment, the TBA is added to the liquid composition comprising the antibody immediately prior to freezing the liquid antibody/TBA mixture. In certain embodiments, the antibody is a full length antibody. In one embodiment, the antibody is a monoclonal antibody. In one embodiment, the antibody is a human monoclonal antibody. In one embodiment, the antibody is a humanized monoclonal antibody. In one embodiment, the antibody is a chimeric antibody. In one embodiment, the antibody is an antibody fragment. In one embodiment, the antibody is an antigen-binding fragment, such as a Fv, Fab, Fab', Fab'-SH, F(ab')$_2$; diabodies; linear antibodies; single-chain antibody molecules (e.g. scFv); and multispecific antibodies formed from antibody fragments. In one embodiment, the antibody is a bispecific antibody. In one embodiment, the antibody is an antibody-drug conjugate (e.g., an immunoconjugate). In some embodiments, the sugar is sucrose or trehalose. In certain embodiments, the addition of TBA to the liquid composition has no effect on the integrity or stability of the antibody.

In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, wherein the concentration of the antibody in the liquid composition comprising the antibody is between about 10 mg/ml to about 250 mg/ml, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent, wherein the time for reconstituting the antibody lyophilized in the presence of TBA is less than the time for reconstituting the same amount of the same antibody lyophilized in the absence of TBA. In some embodiments, the amount of TBA added to the liquid antibody composition to form the liquid antibody/TBA mixture is about 5%-6% by volume. In some embodiments, the concentration of the antibody in the liquid composition comprising the antibody is between about 25 mg/ml to about 250 mg/ml, between about 50 mg/ml to about 250 mg/ml, between about 100 mg/ml to about 250 mg/ml, between about 150 mg/mml to about 250 mg/ml, between about 25 mg/ml to about 100 mg/ml, between about 50 mg/ml to about 100 mg/ml, between about 25 mg/ml to about 125 mg/ml, or between about 50 mg/ml to about 125 mg/ml. In some embodiments, the concentration of the antibody in the liquid composition comprising the antibody is about 25 mg/ml, about 40 mg/ml, about 50 mg/ml, about 60 mg/ml, about 70 mg/ml, about 100 mg/ml, about 125 mg/ml, about 150 mg/ml, about 200 mg/ml, or about 250 mg/ml. In some embodiments, the sugar is sucrose or trehalose. In certain embodiments, the addition of TBA to the liquid composition has no effect on the integrity or stability of the antibody.

In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, wherein the amount of the antibody in the liquid composition comprising the antibody is between about 150 mg to about 11 grams, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent, wherein the time for reconstituting the antibody lyophilized in the presence of TBA is less than the time for reconstituting the same amount of the same antibody lyophilized in the absence of TBA. In some embodiments, the amount of TBA added to the liquid antibody composition to form the liquid antibody/TBA mixture is about 5%-6% by volume. In some embodiments, the amount of the antibody in the liquid composition comprising the antibody is about 150 mg, about 250 mg, about 500 mg, about 750 mg, about 1 gram, about 2 grams, about 3 grams, about 4 grams, about 5 grams, about 6 grams, about 7 grams, about 8 grams, about 9 grams, about 10 grams, or about 11 grams. In some embodiments, the amount of the antibody in the liquid composition comprising the antibody is between about 150 mg to about 1 gram, between about 500 mg to about 1 gram, between about 500 mg to about 5 grams, between about 1 gram to about 5 grams, between about 1 gram to about 10 grams, or between about 5 grams to about 10 grams. In some embodiments, the quantity of the antibody in the liquid composition comprising the antibody is greater than 11 grams. In some embodiments, the sugar is a sucrose or trehalose. In certain embodiments, the addition of TBA to the liquid composition has no effect on the integrity or stability of the antibody.

In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent, wherein the time for reconstituting the antibody lyophilized in the presence of TBA is less than the time for reconstituting the same amount of the same antibody lyophilized in the absence of TBA, wherein the time for reconstituting the lyophilized antibody composition which was lyophilized in the presence of TBA is reduced by about 40% to about 95% compared to the time for reconstituting the same amount of the same antibody composition lyophilized in the absence of TBA. In some embodiments, the amount of TBA added to the liquid antibody composition to form the liquid antibody/TBA mixture is about 5%-6% by volume. In some embodiments, the time for reconstituting the lyophilized antibody composition which was lyophilized in the presence of TBA is reduced by about 40%, by about 50%, about 60%, about 70%, about 80%, about 90%, about 95%, about 50% to about 60%, about 60% to about 70%, about 70% to about 80%, about 80% to about 90%, or about 90% to about 95% compared to the time for reconstituting the same amount of the same antibody composition lyophilized in the absence of TBA. In some embodiments, the sugar is sucrose or trehalose. In certain embodiments, the addition of TBA to the liquid composition has no effect on the integrity or stability of the antibody.

In some embodiments of the present invention, the liquid antibody/TBA mixture is lyophilized in a vial, a syringe (including dual-chamber syringe), or a cartridge. In some embodiments, the liquid antibody/TBA mixture is lyophilized in a glass vial. In some embodiments, the vial is a 6 cc vial, a 10 cc vial, a 15 cc vial, a 20 cc vial, a 50 cc vial, or a 100 cc vial. In some embodiments, the vials have a capacity or fill volume of 0.1 ml, 0.3 ml, 0.5 ml, 1 ml, 2 ml, 2.5 ml, 5 ml, 10 ml, 20 ml, 25 ml, 50 ml, or 100 ml.

In some embodiments, reconstituting the lyophilized antibody composition is performed under conditions in which reconstituting the lyophilized antibody composition is performed under a vacuum. In some embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent, wherein the reconstituting the lyophilized antibody composition is performed under conditions in which the lyophilized antibody composition is under a vacuum, and further wherein the time for reconstituting the antibody lyophilized in the presence of TBA is less than the time for reconstituting the same amount of the same antibody lyophilized in the absence of TBA. In some embodiments, the amount of TBA added to the liquid antibody composition to form the liquid antibody/TBA mixture is about 5%-6% by volume. In some embodiments, the vacuum is a deep vacuum. In some embodiments, the vacuum is a partial vacuum. In certain embodiments, the vacuum is less than 100 Torr. In certain embodiments, the vacuum is less than 50 Torr. In certain embodiments, the vacuum is between 100 mTorr and 50 Torr. In one embodiment, the vacuum is at 100 mTorr.

In some embodiments, reconstituting the lyophilized antibody composition is performed using a shaker, such as a mechanical shaker. In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent by using a shaker, wherein the time for reconstituting the antibody lyophilized in the presence of TBA is less than the time for reconstituting the same amount of the same antibody lyophilized in the absence of TBA. In some embodiments, the vial or container is placed on the shaker. In some embodiments, the amount of TBA added to the liquid antibody composition to form the liquid antibody/TBA mixture is about 5%-6% by volume.

In some embodiments, reconstituting the lyophilized antibody composition is performed under conditions in which the lyophilized antibody composition is under a vacuum and using a shaker. In one embodiment, the present invention provides a method for reducing the reconstitution time of a lyophilized antibody composition, wherein the method comprises preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, and reconstituting the lyophilized antibody composition with a diluent by using a shaker, wherein the reconstituting the lyophilized antibody composition is performed under conditions in which the lyophilized antibody composition is under a vacuum, and further wherein the time for reconstituting the antibody lyophilized in the presence of TBA is less than the time for reconstituting the same amount of the same antibody lyophilized in the absence of TBA. In some embodiments, the vacuum is a deep vacuum. In some embodiments, the vacuum is a partial vacuum. In certain embodiments, the vacuum is less than 100 Torr. In certain embodiments, the vacuum is less than 50 Torr. In certain embodiments, the vacuum is between 100 mTorr and 50 Torr. In one embodiment, the vacuum is at 100 mTorr. In some embodiments, the amount of TBA added to the liquid antibody composition to form the liquid antibody/TBA mixture is about 5%-6% by volume.

The steps of the methods of the present disclosure may be performed by one person or entity, or the steps may be performed by multiple people or by multiple entities. The steps may be performed by multiple people or multiple entities at the direction of one person or one entity. For example, one person or entity may prepare the liquid composition comprising the polypeptide and a sugar, and a different person or entity may add TBA to the liquid composition to form a liquid polypeptide/TBA mixture prior to freezing the liquid polypeptide/TBA mixture. In another example, one person or entity may lyophilize the liquid polypeptide/TBA mixture to form a lyophilized polypeptide composition, and a different person or entity may reconstitute the lyophilized polypeptide composition with a diluent.

Accordingly, in one aspect, the present invention provides a method for reducing the reconstitution time of a lyophilized polypeptide or antibody composition, wherein the method comprises adding tert-butyl alcohol (TBA) to a liquid composition comprising the polypeptide or antibody and a sugar at a molar ratio of at least about 360:1 to form a liquid polypeptide or antibody/TBA mixture, wherein the amount of TBA in the liquid polypeptide or antibody/TBA mixture is about 5%-20% by volume, freezing the liquid polypeptide or antibody/TBA mixture, lyophilizing the liquid polypeptide or antibody/TBA mixture to form a lyophilized polypeptide or antibody composition, and reconstituting the lyophilized polypeptide or antibody composition with a diluent, wherein the time for reconstituting the polypeptide or antibody lyophilized in the presence of TBA is less than the time for reconstituting the same amount of the same polypeptide or antibody lyophilized in the absence of TBA. In some embodiments, the amount of TBA in the liquid polypeptide or antibody/TBA mixture is about 5%-6% by volume.

In another aspect, the present invention provides a method for reducing the reconstitution time of a lyophilized polypeptide or antibody composition, wherein the method comprises adding tert-butyl alcohol (TBA) to a liquid composition comprising the polypeptide or antibody and a sugar at a molar ratio of at least about 360:1 to form a liquid polypeptide or antibody/TBA mixture, wherein the amount of TBA in the liquid polypeptide or antibody/TBA mixture is about 5%-20% by volume, freezing the liquid polypeptide or antibody/TBA mixture, and lyophilizing the liquid polypeptide or antibody/TBA mixture to form a lyophilized polypeptide or antibody composition, wherein the lyophilized polypeptide or antibody composition is subsequently reconstituted with a diluent, wherein the time for reconstituting the polypeptide or antibody lyophilized in the presence of TBA is less than the time for reconstituting the same amount of the same polypeptide or antibody lyophilized in the absence of TBA. In some embodiments, the amount of TBA in the liquid polypeptide or antibody/TBA mixture is about 5%-6% by volume.

The present invention provides liquid antibody formulations suitable for lyophilization. In some embodiments, the present invention provides liquid antibody formulations suitable for lyophilization, wherein the formulation comprises the antibody, a sugar, a diluent, and TBA, wherein the amount of TBA in the liquid formulation is between about 5%-20% by volume, wherein the amount of sugar in the liquid formulation is at a molar ratio of sugar:antibody of at least about 360:1, and wherein the time for reconstituting the antibody lyophilized in the presence of TBA is less than the time for reconstituting the same amount of the same antibody lyophilized in the absence of TBA. In some embodiments, the amount of TBA in the liquid formulation is selected from the group consisting of 5%, 7.5%, 10%, 12.5%, 15%, 17.5%, and 20% by volume. In other embodiments, the amount of TBA added to the liquid antibody composition to form the liquid antibody/TBA mixture is between about 5% to about 10% by volume. In some embodiments, the amount of TBA in the liquid formulation is about 5%-6% by volume. In one embodiment, the TBA is added to the liquid composition comprising the antibody immediately prior to freezing the liquid antibody/TBA mixture. In some embodiments, the sugar is sucrose or trehalose. In certain embodiments, the presence of TBA in the liquid antibody formulation has no effect on the integrity or stability of the antibody.

The present invention provides a lyophilized antibody composition, wherein the lyophilized antibody composition is produced by preparing a liquid composition comprising the antibody and a sugar at a molar ratio of sugar:antibody of at least about 360:1, adding tert-butyl alcohol (TBA) to the liquid composition to form a liquid antibody/TBA mixture, wherein the amount of TBA in the liquid antibody/TBA mixture is between about 5%-20% by volume, freezing the liquid antibody/TBA mixture, lyophilizing the liquid antibody/TBA mixture to form a lyophilized antibody composition, wherein upon reconstitution of the lyophilized antibody composition with a diluent, the time for reconstituting the antibody lyophilized in the presence of TBA is less than the time for reconstituting the same amount of the same antibody lyophilized in the absence of TBA. In some embodiments, the amount of TBA in the liquid formulation is selected from the group consisting of 5%, 7.5%, 10%, 12.5%, 15%, 17.5%, and 20% by volume. In other embodiments, the amount of TBA added to the liquid antibody composition to form the liquid antibody/TBA mixture is between about 5% to about 10% by volume. In some embodiments, the amount of TBA added to the liquid antibody composition to form the liquid antibody/TBA mixture is between about 5% to about 6% by volume. In one embodiment, the TBA is added to the liquid composition comprising the antibody immediately prior to freezing the liquid antibody/TBA mixture. In some embodiments, the sugar is sucrose or trehalose. In certain embodiments, the addition of TBA to the liquid composition has no effect on the integrity or stability of the antibody in the liquid composition or in the lyophilized antibody composition.

BRIEF DESCRIPTION OF THE DRAWINGS

FIG. 10A shows results for mAb1, and FIG. 10B shows results for mAb2.

DETAILED DESCRIPTION OF THE INVENTION

Figure 1:
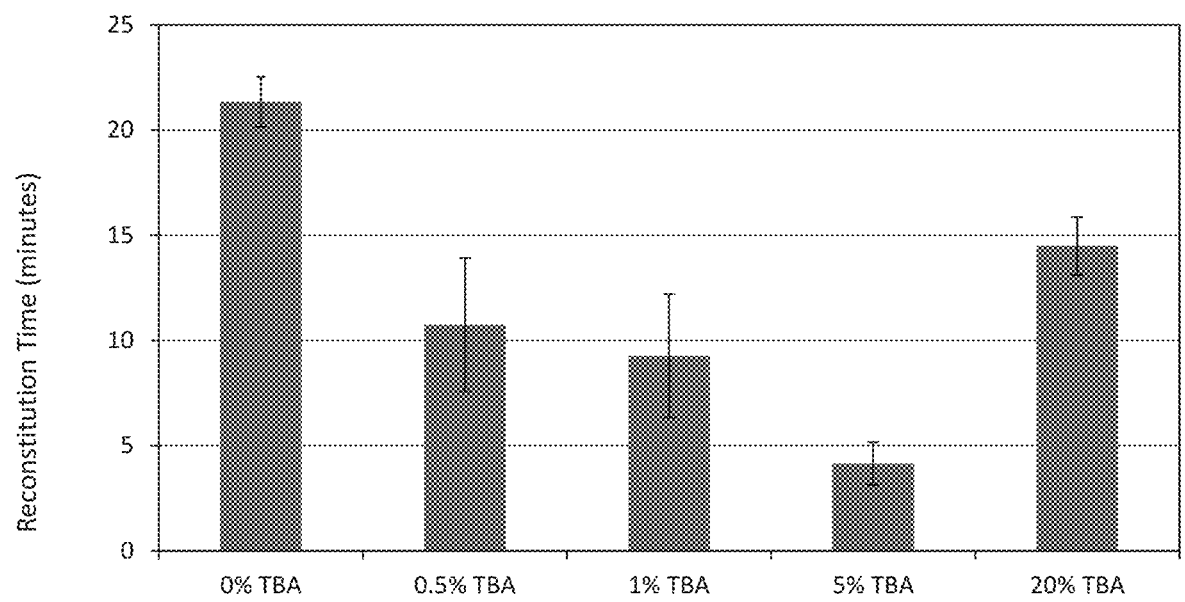
FIG. 1 sets forth data showing reconstitution times for a lyophilized antibody formulation containing 0%, 0.5%, 1%, 5%, and 20% (v/v) tert-butyl alcohol.

The present invention provides, inter alia, polypeptide formulations, lyophilization formulations, methods of making lyophilization formulations, and methods and formulations useful for reducing reconstitution time of a lyophilized polypeptide.

Definitions

The term "antibody" herein is used in the broadest sense and encompasses various antibody structures, including but not limited to monoclonal antibodies, polyclonal antibodies, multi-specific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "immunoconjugate" is an antibody conjugated to one or more heterologous molecule(s), including but not limited to a cytotoxic agent.

An "antibody-drug conjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, cryo protectant (e.g., sucrose, trehalose), or preservative. A pharmaceutically acceptable carrier or diluent includes sterile water for injection.

As used herein, "reconstitution time" and grammatical variations thereof refer to the amount of time necessary for a lyophilized molecule to be dissolved and/or suspended in a liquid form. For example, reconstitution time includes, but is not limited to, the time required for a dried (i.e., lyophilized) pellet or cake of a polypeptide to become suspended in water or a buffer following lyophilization. A "reduction" or "reducing" or "reduced" reconstitution time and grammatical variations thereof means less time is required for an amount of a polypeptide lyophilized under a first formulation and/or condition to suspend in a liquid compared with the same amount of the same polypeptide lyophilized under a second formulation and/or condition and suspended in the same liquid.

As used herein, the term "cake" or "lyophilized cake" or "lyo cake" refers to a freeze-dried (i.e., lyophilized) polypeptide composition or formulation.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

Pharmaceutical Formulations

Pharmaceutical formulations of an antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer. In certain embodiments, an antibody formulation of the present invention comprises a liquid antibody composition and TBA, wherein the TBA is added to the liquid antibody composition prior to lyophilization. In some aspects, an antibody formulation of the present invention comprises an amount of TBA in the liquid antibody composition selected from the group consisting of 0.5%, 1%, 2.5%, 5%, 7.5%, 10%, 12.5%, 15%, 17.5%, and 20% by volume. In other embodiments, the amount of TBA in the liquid antibody composition is between about 1% to about 20% by volume, between about 1% to about 10% by volume, between about 1% to about 5% by volume, between about 5% to about 20% by volume, or between about 5% to about 10% by volume.

In some embodiments, antibody compositions and formulations of the present disclosure comprise the antibody and a sugar at a molar ratio of sugar:antibody of at least about 360:1. In some embodiments, the molar ratio of sugar:antibody is at least about 360:1, at least about 380:1, at least about 400:1, at least about 420:1, at least about 440:1, at least about 460:1, at least about 480:1, or at least about 500:1, including every value in between these numbers. In some embodiments, the ratio is between about 360:1 and about 500:1. The sugar may be sucrose or trehalose or any other sugar known in the art to improve the stability of proteins during lyophilization. As used herein, the weight of trehalose in the formulation for calculating the weight ratio of the antibody to the trehalose is based on the amount of trehalose anhydrous (MW 342.30). If other forms of trehalose (e.g., trehalose dihydrate) are used, the weight of the trehalose in the formulation should be converted from the weight of trehalose dihydrate with the same molar concentration. When calculating the molar ratio of sugar:antibody, a molecular weight of 150 kDa may be assumed for the antibody.

The formulation herein may also contain more than one active ingredients as necessary for the particular indication being treated, preferably those with complementary activities that do not adversely affect each other. Such active ingredients are suitably present in combination in amounts that are effective for the purpose intended.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

The present invention provides, inter alia, polypeptide formulations, lyophilization formulations, and methods for reducing the reconstitution time of a lyophilized polypeptide composition. Lyophilization methodologies and techniques are well-known in the art. Generally, the process of lyophilization is as follows: A dissolved substance (e.g., biological molecule, polypeptide) is frozen in its final package or storage container (e.g., vial, syringe, or cartridge) at a low temperature (e.g., −60° C.). Lyophilization, or freeze drying, is a process in which water is removed from a product after it is frozen and placed under vacuum, allowing the ice to change directly from solid to vapor without passing through a liquid phase. The process involves three separate and interdependent processes: freezing, primary drying (sublimation), and secondary drying (desorption). What results is a dry lyophilization cake (i.e., a dry lyo cake), the structure of which, including its density, pore size, total pore volume, and surface area are controlled by production (e.g., diluent, temperature, vacuum strength, drying conditions, freezing conditions, etc.). With proper storage, lyophilized biological molecules and polypeptides typically remain stable for 2 or 3 years.

Lyophilization containers include, for example, vials, syringes, or cartridges. Numerous lyophilization containers of various sizes are commercially available, many of which are made of glass. Vial sizes for use in lyophilization include, but are not limited to, 6 cc vials, 10 cc vials, 15 cc vials, 20 cc vials, 50 cc vials, 100 cc vials, etc. Lyophilization vials of various capacities (or fill volumes) are also available, including vials having a capacity or fill volume of 0.1 ml, 0.3 ml, 0.5 ml, 1 ml, 2 ml, 2.5 ml, 5 ml, 10 ml, 20 ml, 25 ml, 50 ml, 100 ml, etc.

The present invention provides a method for reducing reconstitution time of a lyophilized polypeptide composition, the method comprising: (a) preparing a liquid composition comprising the polypeptide, (b) adding tert-butyl alcohol (TBA) to the liquid composition to form a liquid polypeptide/TBA mixture, (c) freezing the liquid polypeptide/TBA mixture, (d) lyophilizing the liquid polypeptide/TBA mixture to form a lyophilized polypeptide composition (i.e., a lyophilized polypeptide cake), (e) reconstituting the lyophilized polypeptide composition with a diluent, wherein the time for reconstituting the polypeptide lyophilized in the presence of TBA is less than the time for reconstituting the same amount of the same polypeptide lyophilized in the absence of TBA.

The present invention provides methods and formulations for reducing reconstitution time of a lyophilized polypeptide composition in which TBA is added to a liquid composition comprising the polypeptide prior to lyophilization. In certain embodiments, the amount of TBA added to the liquid composition comprising the polypeptide is from about 0.5% by volume to about 20% by volume, from about 1% by volume to about 20% by volume, from about 1% by volume to about 10% by volume, from about 1% by volume to about 5% by volume, from about 5% by volume to about 20% by volume, from about 5% by volume to about 10% by volume, or from about 10% by volume to about 20% by volume.

In other embodiments, the amount of TBA added to the liquid composition comprising the polypeptide is about 0.5%, 1%, 2.5%, 5%, 7.5%, 10%, 12.5%, 15%, 17.5%, or 20% by volume. In one embodiment, the amount of TBA added to the liquid composition comprising the polypeptide is about 5%-6% by volume. In one embodiment, the amount of TBA added to the liquid composition comprising the polypeptide is about 5% by volume. In one embodiment, the amount of TBA added to the liquid composition comprising the polypeptide is 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.1%, or 6.2%. In one embodiment, the amount of TBA added to the liquid composition comprising the polypeptide is about 10% by volume. In one embodiment, the amount of TBA added to the liquid composition comprising the polypeptide is about 20% by volume.

The methods and formulations of the present invention are effective at reducing the reconstitution time of various concentrations of a polypeptide, an in particular, useful and effective at reducing the reconstitution time of high-concentration polypeptide compositions. For example, the present invention provides methods and formulations effective at reducing reconstitution time of a lyophilized polypeptide composition by adding TBA to a liquid composition comprising the polypeptide prior to lyophilization, in which the liquid composition comprising the polypeptide has a high polypeptide concentration. In certain embodiments, the concentration of the polypeptide in the liquid composition comprising the polypeptide is between about 10 mg/ml and 250 mg/ml. In certain embodiments, the concentration of the polypeptide in the liquid composition comprising the polypeptide is between about 25 mg/ml to about 250 mg/ml, between about 50 mg/ml to about 250 mg/ml, between about 100 mg/ml to about 250 mg/ml, between about 150 mg/mml to about 250 mg/ml, between about 25 mg/ml to about 100 mg/ml, between about 50 mg/ml to about 100 mg/ml, between about 25 mg/ml to about 125 mg/ml, or between about 50 mg/ml to about 125 mg/ml. In some embodiments, the concentration of the polypeptide in the liquid composition comprising the polypeptide is about 25 mg/ml, about 40 mg/ml, about 50 mg/ml, about 60 mg/ml, about 70 mg/ml, about 100 mg/ml, about 125 mg/ml, about 150 mg/ml, about 200 mg/ml, or about 250 mg/ml.

The methods and formulations of the present invention are effective at reducing the reconstitution time of various amounts and quantities of a polypeptide. For example, the present invention provides methods and formulations effective at reducing reconstitution time of a lyophilized polypeptide composition by adding TBA to a liquid composition comprising the polypeptide prior to lyophilization, in which the liquid composition comprising the polypeptide has a large quantity or amount of the polypeptide. In certain embodiments, the amount of the polypeptide in the liquid composition comprising the polypeptide is between about 150 mg to about 11 grams. In certain embodiments, the quantity of the polypeptide in the liquid composition comprising the polypeptide (and following lyophilization) is about 150 mg, about 250 mg, about 500 mg, about 750 mg, about 1 gram, about 2 grams, about 3 grams, about 4 grams, about 5 grams, about 6 grams, about 7 grams, about 8 grams, about 9 grams, about 10 grams, or about 11 grams. In some embodiments, the quantity of the polypeptide in the liquid composition comprising the polypeptide is greater than 11 grams.

Swirling or shaking the lyophilization container can further improve the reconstitution time of a lyophilized polypeptide. In some embodiments of the present invention, reconstituting the lyophilized polypeptide is performed by adding a diluent to the lyophilized polypeptide in the lyophilization container and swirling the container (either periodically or continuously) until the lyophilized polypeptide is dissolved or suspended in the diluent. In other embodiments of the present invention, reconstituting the lyophilized polypeptide is performed by adding a diluent to the lyophilized polypeptide in the lyophilization container and placing the container on a shaker (e.g., a mechanical shaker) and shaking the lyophilization container until the lyophilized polypeptide is dissolved or suspended in the diluent.

Reconstitution of the polypeptide under vacuum can also improve the reconstitution time of a lyophilized polypeptide. In some embodiments of the present invention, the lyophilization container comprising the lyophilized polypeptide is maintained under a vacuum during reconstitution. In one embodiment, the lyophilization container comprising the lyophilized polypeptide is under full vacuum during reconstitution. In certain embodiments, the lyophilization container comprising the lyophilized polypeptide is at less than 100 Torr during reconstitution. In certain embodiments, the lyophilization container comprising the lyophilized polypeptide is at less than 50 Torr during reconstitution. In certain embodiments, the lyophilization container comprising the lyophilized polypeptide is between 100 mTorr and 50 Torr. In one embodiment, the lyophilization container comprising the lyophilized polypeptide is at 100 mTorr.

The present invention provides lyophilized polypeptide compositions produced by a method of the present invention. In some embodiments, the present invention provides a lyophilized polypeptide composition, wherein the lyophilized polypeptide composition is produced by preparing a liquid composition comprising the polypeptide, adding tert-butyl alcohol (TBA) to the liquid composition to form a liquid polypeptide/TBA mixture, freezing the liquid polypeptide/TBA mixture, lyophilizing the liquid polypeptide/TBA mixture to form a lyophilized polypeptide composition, wherein upon reconstitution of the lyophilized polypeptide composition with a diluent, the time for reconstituting the polypeptide lyophilized in the presence of TBA is less than the time for reconstituting the same amount of the same polypeptide lyophilized in the absence of TBA. In certain embodiments, the lyophilized polypeptide composition is a lyophilized cake comprising the polypeptide.

The present invention provides liquid polypeptide compositions produced by a method of the present invention. In some embodiments, the present invention provides a liquid polypeptide composition, wherein the liquid polypeptide composition is produced by preparing a liquid composition comprising the polypeptide, and adding tert-butyl alcohol (TBA) to the liquid composition to form a liquid polypeptide/TBA mixture, wherein upon the liquid polypeptide/TBA mixture to form a lyophilized polypeptide composition and subsequent reconstitution of the lyophilized polypeptide composition with a diluent, the time for reconstituting the polypeptide lyophilized in the presence of TBA is less than the time for reconstituting the same amount of the same polypeptide lyophilized in the absence of TBA.

In some embodiments of the present disclosure, the addition of TBA to the liquid composition comprising an antibody and a sugar at a molar ratio of sugar:antibody of at least about 360:1, wherein the amount of TBA in the liquid antibody/TBA mixture is between about 5%-20% by volume, has no effect on the integrity or stability of the antibody in the liquid antibody/TBA mixture, in the lyophilized antibody composition, or in the liquid antibody formulation suitable for lyophilization. In such embodiments, the antibody essentially retains its physical stability and/or chemical stability and/or biological activity upon storage in a liquid composition or in a lyophilized composition. Preferably, the antibody in the compositions and formulations provided herein essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period.

In certain embodiments, the liquid antibody formulation suitable for lyophilization is stable at about 40° C. for at least about 1, 2, 3, 4, 5, 6, 7, 14, 21, 28, or more days. In certain embodiments, the liquid antibody formulation is stable at about 40° C. for at least about 1, 2, 3, 4, 5, 6, 7, 8, or more weeks. In certain embodiments, the liquid antibody formulation is stable at about 25° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the liquid antibody formulation is stable at about 5° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the liquid antibody formulation is stable at about −20° C. or lower for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. Furthermore, the liquid antibody formulation is preferably stable following freezing (to, e.g., −20° C., −40° C. or −70° C.) and thawing of the liquid antibody formulation, for example following 1, 2 3, 4, or 5 cycles of freezing and thawing.

In certain embodiments, the lyophilized antibody composition is stable at about 25° C. for at least 1, 2, 3, 4, 5, 6, 7, 8, or more weeks, or for at least 1, 2, 3, 4, 5, 6, 7, 8, 9, 10, 11, 12, 13, 14, 15, 16, 17, 18, 19, 20, 21, 22, 23, 24, or more months. In certain embodiments, the lyophilized antibody composition is stable at about 5° C. for at least 1, 2, 3, 4, 5, 6, 7, 8, 9, 10, 11, 12, 13, 14, 15, 16, 17, 18, 19, 20, 21, 22, 23, 24, or more months. In certain embodiments, the lyophilized antibody composition is stable at about −20° C. or lower for at least 1, 2, 3, 4, 5, 6, 7, 8, 9, 10 or more years.

Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

An antibody "retains its physical stability" in a composition or pharmaceutical formulation if it shows no signs or very little of aggregation, precipitation and/or denaturation upon visual examination of color and/or clarity, or as measured by methods known in the art, such as, for example, UV light scattering or by size exclusion chromatography.

An antibody "retains its chemical stability" in a composition or pharmaceutical formulation, if the chemical stability at a given time is such that the antibody is considered to still retain its biological activity as defined below. Chemical stability can be assessed, for example, by detecting and quantifying chemically altered forms of the antibody. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography or icIEF, for example.

An antibody "retains its biological activity" in a composition or pharmaceutical formulation, if the biological activity of the antibody at a given time is within about 10% (within the errors of the assay) of the biological activity exhibited at the time the composition or pharmaceutical formulation was prepared as determined in an antigen binding assay, for example. Other "biological activity" assays for antibodies are elaborated herein below.

As used herein, "biological activity" of a monoclonal antibody refers to the ability of the antibody to bind to antigen. It can further include antibody binding to antigen and resulting in a measurable biological response which can be measured in vitro or in vivo. Such activity may be antagonistic or agonistic.

Antibodies

Exemplary techniques for producing antibodies which can be formulated according to the present invention are provided herein. In one embodiment, the antigen to which the antibody binds is a biologically important protein and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated.

Where the antigen is a polypeptide, it may be a transmembrane molecule (e.g., receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-b1, TGF-b2, TGF-b3, TGF-b4, or TGF-b5; a tumor necrosis factor (TNF) such as TNF-alpha or TNF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD22 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9 and IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Exemplary molecular targets for antibodies encompassed by the present invention include CD proteins such as CD3, CD4, CD8, CD19, CD20, CD22, CD34 and CD40; members of the ErbB receptor family such as the EGF receptor, HER2, HER3 or HER4 receptor; B cell surface antigens, such as CD20 or BR3; a member of the tumor necrosis receptor superfamily, including DR5; prostate stem cell antigen (PSCA); cell adhesion molecules such as LFA-1, Mad, p150.95, VLA-4, ICAM-1, VCAM, alpha4/beta7 integrin, and alphav/beta3 integrin including either alpha or beta subunits thereof (e.g. anti-CD11a, anti-CD 18 or anti-CD 11b antibodies); growth factors such as VEGF as well as receptors therefor; tissue factor (TF); a tumor necrosis factor (TNF) such as TNF-alpha or TNF-beta, alpha interferon (alpha-IFN); an interleukin, such as IL-8; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Exemplary antibodies which can be formulated according to the present invention include, but are not limited to the following: anti-ErbB antibodies, including anti-HER2 antibodies (e.g. trastuzumab (HERCEPTIN®) or pertuzumab); antibodies that bind to a B-cell surface marker, such as CD20 (for example rituximab and humanized 2H7/ocrelizumab), CD22, CD40 or BR3; antibodies that bind to IgE, including omalizumab (XOLAIR®) commercially available from Genentech, E26, HAE1, IgE antibody with an amino acid substitution at position 265 of an Fc region thereof (US 2004/0191244 A1), Hu-901, an IgE antibody as in WO2004/070011, or antibody that binds the small extracellular segment on IgE, Ml' (e.g. 47H4v5; see U.S. Pat. No. 8,071,097), see, also, Presta et al, J. Immunol. 151:2623-2632 (1993); International Publication No. WO 95/19181; U.S. Pat. No. 5,714,338, issued Feb. 3, 1998; U.S. Pat. No. 5,091,313, issued Feb. 25, 1992; WO 93/04173 published Mar. 4, 1993; WO 99/01556 published Jan. 14, 1999; and U.S. Pat. No. 5,714,338; antibodies that bind to vascular endothelial growth factor (VEGF) (e.g. bevacizumab) or a VEGF receptor; anti-IL-8 antibodies (St John et al, Chest, 103:932 (1993), and International Publication No. WO 95/23865); anti-PSCA antibodies (WO01/40309); anti-CD40 antibodies, including S2C6 and humanized variants thereof (WO00/75348); anti-CD1 1a antibodies, including efalizumab (RAPTIVA®) (U.S. Pat. No. 5,622,700, WO 98/23761, Steppe et al, Transplant Intl. 4:3-7 (1991), and Hourmant et al, Transplantation 58:377-380 (1994)); anti-CD18 antibodies (U.S. Pat. No. 5,622,700, issued Apr. 22, 1997, or as in WO 97/26912, published Jul. 31, 1997); anti-Apo-2 receptor antibody (WO 98/51793 published Nov. 19, 1998); anti-TNF-alpha antibodies including cA2 (REMICADE®) and adalimumab (HUMIRA®), CDP571 and MAK-195 (Afelimomab) (See, U.S. Pat. No. 5,672,347 issued Sep. 30, 1997, Lorenz et al. J. Immunol. 156(4): 1646-1653 (1996), and Dhainaut et al. Crit. Care Med. 23(9): 1461-1469 (1995)); anti-Tissue Factor (TF) (European Patent No. 0 420 937 B1 granted Nov. 9, 1994); anti-human a4137 integrin (WO 98/06248 published Feb. 19, 1998); anti-EGFR antibodies, including chimerized or humanized 225 antibody as in WO 96/40210 published Dec. 19, 1996; anti-CD3 antibodies, such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. Arthritis Rheum 39(1): 52-56 (1996)); anti-CD52 antibodies such as alemtuzumab (CAMPATH-1H®) (Riechmann et al. Nature 332:323-337 (1988); anti-Fc receptor antibodies such as the M22 antibody directed against FcyRI as in Graziano et al. J. Immunol. 155(10):4996-5002 (1995); anti-carcinoembryonic antigen (CEA) antibodies such as hMN-14 (Sharkey et al. Cancer Res. 55(23Suppl): 5935s-5945s (1995); antibodies directed against breast epithelial cells including huBrE-3, hu-Mc 3 and CHL6 (Ceriani et al. Cancer Res. 55(23): 5852s-5856s (1995); and Richman et al. Cancer Res. 55(23 Supp): 5916s-5920s (1995)); antibodies that bind to colon carcinoma cells such as C242 (Litton et al. Eur J. Immunol. 26(1): 1-9 (1996)); anti-CD38 antibodies, e.g. AT 13/5 (Ellis et al. J. Immunol. 155(2):925-937 (1995)); anti-CD33 antibodies such as Hu M195 (Jurcic et al. Cancer Res 55(23 Suppl):5908s-5910s (1995) and CMA-676 or CDP771; anti-CD22 antibodies such as LL2 or LymphoCide (Juweid et al. Cancer Res 55(23 Suppl):5899s-5907s (1995); anti-EpCAM antibodies such as 17-1 A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PR0542; anti-hepatitis antibodies such as the anti-Hep B antibody OSTAVIR®; anti-CA 125 antibody OvaRex; anti-idiotypic GD3 epitope antibody BEC2; anti-avP3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID 10 and the anti-HLA DR antibody Oncolym (Lym-1); anti-CCR5 (PRO 140); ABT-325; ABT-308; ABT-147; anti-beta? (etrolizumab); anti-HER3/EGFR DAF (DL1 If); anti-interleukin 6 receptor (IL6R) such as tocilizumab (ACTEMRA®); anti-FluA (see WO2014/078268) and anti-Abeta (see WO2003/070760 and WO2008/011348), etc.

EXAMPLES

The following are examples of methods and compositions of the invention. It is understood that various other embodiments may be practiced, given the general description provided above.

Example 1. Reconstitution of 2.5 ml and 25 ml mAb Cakes with 0-20% TBA

Purified monoclonal antibody (mAb) solutions (mAb1 and mAb2) were diluted to 70 mg/ml in a buffer containing 168 mM sucrose, 20 mM His-HCl, 0.03% PS20. TBA was warmed above its melting point of 25° C. and then added to the mAb samples as follows. TBA was added directly to the 70 mg/ml mAb solutions for final TBA concentrations of up to 5%. For samples having a final TBA concentration of 10% or 20% (volume/volume), higher initial concentrations of mAb1 (90 mg/mL) and mAb2 (100 mg/mL) were used and diluted to 70 mg/ml protein using 20 mM His buffer containing 168 mM sucrose and 0.03% PS20 following the addition of the appropriate amount of TBA to obtain 10% TBA or 20% TBA (v/v) concentrations in the final mAb solutions.

The mAb/TBA mixtures were then added to washed and depyrogenated Schott tubing vials: 6 cc vials for 2.5 ml fill; 50 cc vials for 25 ml fill. The vials were stoppered with Daikyo D777-1 20 mm lyo stoppers. The vials were then loaded into a laboratory freeze-dryer (Lyostar II, FTS Systems, Stone Ridge, N.Y. or Lyostar III, SP Scientific, Stone Ridge, N.Y.).

Lyophilization was performed as follows. For experiments using uncontrolled nucleation vials were equilibrated at 5° C. for 1 hour. The shelf temperature was then reduced to −35° C. at a rate of −0.3° C./min and held at this temperature for 6 hours.

For experiments using controlled nucleation, vials were equilibrated at −10° C. for 2 hours. The chamber was pressurized to 28.5 psig with nitrogen for 5 minutes and then depressurized over ~2 seconds. The shelf temperature was then reduced to −35° C. at a rate of −0.3° C./min and held at this temperature for 6 hours. All vial samples in a given experiment were consolidated in one lyophilizer for drying in order to avoid any possible inter-lyophilizer variability in drying behavior. Primary drying was conducted at a shelf temperature of −10° C. and with a chamber pressure of 100 mTorr until the Pirani gauge converged with the capacitance manometer. Secondary drying (to decrease the moisture in the dried cakes to an acceptable level of 0.5-2%) was conducted at a shelf temperature of 20° C. and with a chamber pressure of 100 mTorr for 12 hours. Following lyophilization, the vials were stored at 5° C.

Lyophilized monoclonal antibody compositions were reconstituted with sterile water for injection (diluent) in amounts sufficient to produce solutions having mAb protein concentrations identical to the protein concentrations prior to lyophilization. 2.2 ml of sterile water for injection was added to each 6 cc vial which originally contained 2.5 ml fill; 22 ml of sterile water for injection was added to each 50 cc vial which originally contained 25 ml fill. Prior to reconstitution, vials and the sterile water for injection (reconstitution diluent) were allowed to equilibrate at room temperature.

Reconstitution of mAb1 in 6 cc vials was performed by adding 2.2 ml sterile water for injection and swirled for 5 seconds; after which the vials were placed on an orbital shaker at 60 rpm until the antibody solution was fully reconstituted (i.e., complete dissolution). Reconstitution of mAb2 in 6 cc vials was performed by adding 2.2 ml sterile water for injection and swirled for 5 seconds; after which the vials were manually swirled for 5 seconds every 10 minutes until the antibody solution was fully reconstituted. Reconstitution of mAb1 in 50 cc vials was performed by adding 22 ml sterile water for injection and swirled for 5 seconds; after which the vials were swirled for 5 seconds every 10 minutes until the antibody solution was fully reconstituted.

Vials containing samples for manual reconstitution were swirled for 5 seconds immediately following the addition of diluent and then swirled approximately every ten minutes until the remaining solid was confirmed to be dissolved by visual inspection. Agitation was stopped occasionally to visually assess remaining solid.

FIG. 1 shows the effect of different concentrations of TBA on reconstitution time (minutes) of lyophilized mAb1 from the 6 cc vials (2.5 ml fill). As shown in FIG. 1, the addition of 0.5%, 1%, 5%, or 20% TBA to the antibody solution prior to lyophilization resulted in a reduction in reconstitution time of mAb1. In particular, the addition of 5% TBA reduced reconstitution time of the lyophilized antibody from greater than 20 minutes to less than 5 minutes, an approximately 80% reduction in reconstitution time compared to non-TBA treated control.

Table 1 below shows the specific reconstitution times associated with the above-described experiment for three separate 6 cc vials for each TBA concentration tested.

TABLE 1

| | Reconstitution Time (minutes) | | | | |
|---|---|---|---|---|---|
| TBA Amount | Vial A | Vial B | Vial C | Average | Standard Deviation |
| 0% TBA | 22.18 | 20.5 | ND | 21.34 | 1.19 |
| 0.5% TBA | 7.38 | 11.17 | 13.68 | 10.74 | 3.17 |
| 1% TBA | 6.28 | 9.4 | 12.13 | 9.27 | 2.93 |
| 5% TBA | 5.02 | 4.42 | 3.03 | 4.156 | 1.02 |
| 20% TBA | 14.03 | 13.4 | 14.03 | 14.49 | 1.37 |

Figure 2:
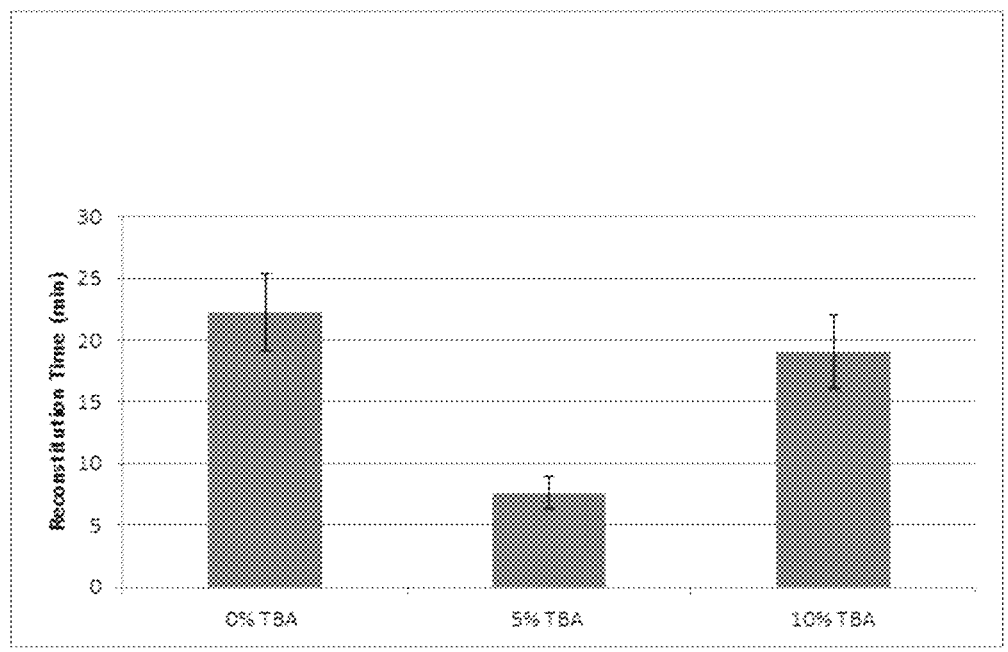
FIG. 2 sets forth data showing reconstitution times for a 2.5 ml lyophilized antibody formulation containing 0%, 5%, and 10% (v/v) tert-butyl alcohol lyophilized in 6 cc vials.

FIG. 2 shows the effect of different concentrations of TBA on reconstitution time (minutes) of lyophilized mAb2 from the 6 cc vials (2.5 ml fill). As shown in FIG. 2, the addition of 5% or 10% TBA to the antibody solution prior to lyophilization resulted in a reduction in reconstitution time of mAb2. In particular, the addition of 5% TBA reduced reconstitution time of the lyophilized antibody from greater than 20 minutes to approximately 7.5 minutes.

Figure 3:
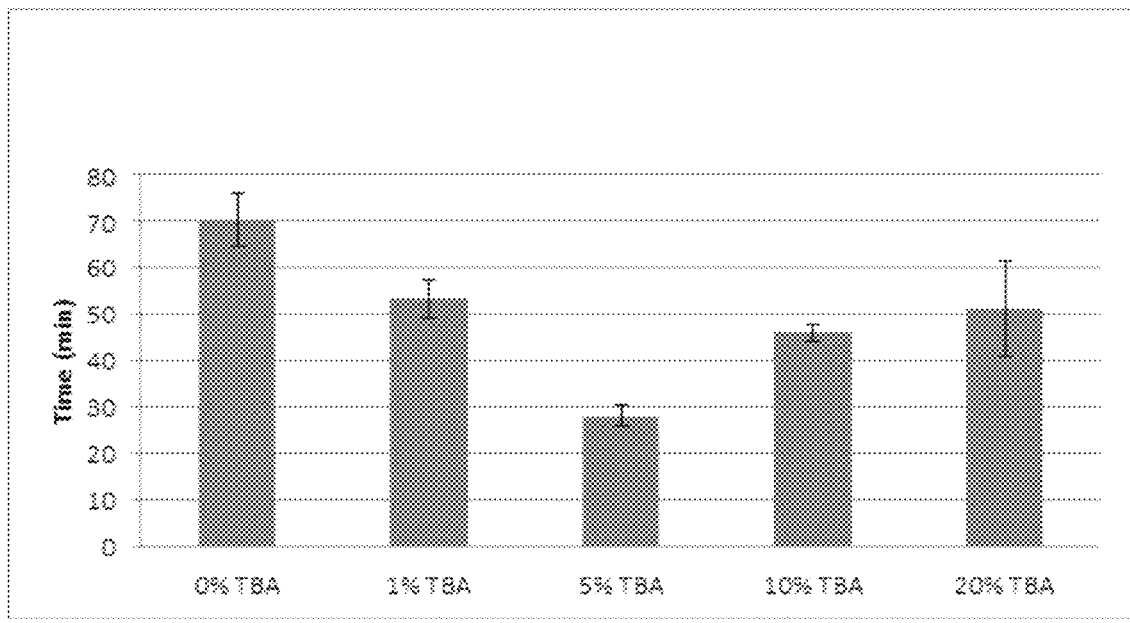
FIG. 3 sets forth data showing reconstitution times for a 25 ml lyophilized antibody formulation containing 0%, 1%, 5%, 10%, and 20% (v/v) tert-butyl alcohol lyophilized in 50 cc vials.

FIG. 3 shows the effect of different concentrations of TBA on reconstitution time (minutes) of lyophilized mAb1 from the 50 cc vials (25 ml fill). As shown in FIG. 3, the addition of 1%, 5%, 10%, or 20% TBA to the antibody solution prior to lyophilization resulted in a reduction in reconstitution time of mAb1. In particular, the addition of 5% TBA reduced reconstitution time of the lyophilized antibody from approximately 70 minutes to approximately 27 minutes.

Taken together, these results showed that addition of TBA to an antibody solution to a prior to lyophilization results in a reduction in reconstitution time. Additionally, these results showed that 5% TBA provides the most reduction in reconstitution time compared to that obtained with 1% TBA, 10% TBA, or 20% TBA.

Example 2. Reconstitution with TBA and Vacuum

The effect on reconstitution time of lyophilized mAb1 under partial vacuum vs full vacuum in combination with TBA was examined as follows. For this study, 100 cc vials were used, containing 60 ml fill volume of mAb1 at 70 mg/ml. TBA was added to the mAb1 solutions to a final concentration of either 5% or 10% TBA. Following lyophilization, vials were backfilled to either 100 mTorr (vacuum) or 200 Torr (partial vacuum control).

Lyophilized mAb1 in the 100 cc vials was reconstituted to the original 60 ml fill volume by addition of sterile water for injection, swirled for 5 seconds, after which the vials were swirled for 5 seconds every 10 minutes until the antibody solution was fully reconstituted (i.e., complete dissolution).

Figure 4:
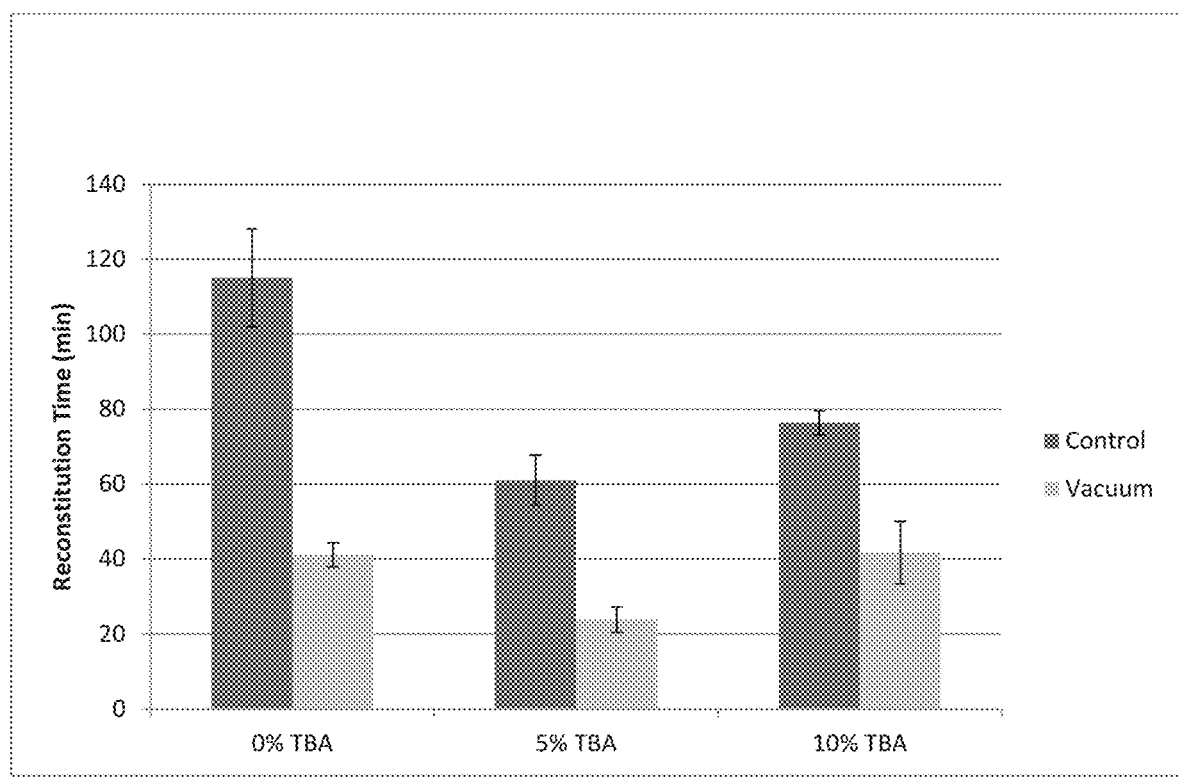
FIG. 4 sets forth data showing the effect of vacuum on reconstitution times for a 60 ml lyophilized antibody formulation containing 0%, 5%, and 10% (v/v) tert-butyl alcohol lyophilized in 100 cc vials.

FIG. 4 shows the effect of different concentrations of TBA (5% and 10% TBA) on reconstitution time of lyophilized mAb1 in 100 cc vials under two different vacuum conditions (either 100 mTorr or 200 Torr). As shown in FIG. 4, the addition of either 5% TBA or 10% TBA to the antibody solution prior to lyophilization resulted in a reduction in reconstitution time of mAb1 in the 100 cc vials with 60 ml fill volume, consistent with the results obtained with either 6 cc or 50 cc vials containing either 2.5 ml fill volume or 25 ml fill volume, respectively. In particular, under 200 Torr conditions, the addition of 5% TBA or 10% TBA reduced reconstitution time from greater than 110 minutes with no TBA to approximately 60 minutes with 5% TBA and to approximately 80 minutes with 10% TBA.

When reconstitutions were performed under 100 mTorr conditions, reconstitution times were greatly reduced. In particular, under 100 mTorr conditions, the addition of 5% TBA or 10% TBA reduced reconstitution times from approximately 40 minutes with no TBA to approximately 20 minutes with 5% TBA and approximately 40 minutes with 10% TBA.

Taken together, these results showed that combining TBA with vacuum showed a greater reduction in reconstitution time compared to using TBA or vacuum alone.

Example 3. Reconstitution with TBA Under Various Shaker Conditions

The effect on reconstitution time of lyophilized mAb1 when reconstitution was performed with or without the aid of a shaker in combination with TBA was examined as follows. For this study, 100 cc vials were used, containing 60 ml fill volume of mAb1 at 70 mg/ml. TBA was added to the mAb1 solutions to a final concentration of either 5% or 10% TBA.

Lyophilized mAb1 in the 100 cc vials was reconstituted to the original 60 ml fill volume by addition of sterile water for injection. Vials containing samples for manual reconstitution were swirled for 5 seconds immediately following the addition of diluent and then swirled approximately every ten minutes until the remaining solid was confirmed to be dissolved by visual inspection. Vials containing samples for reconstitution by shaker were agitated with a Novartis/Genentech 500 rpm Xolair Shaker (South San Francisco, Calif.) following the addition of diluent. Agitation was stopped occasionally to visually assess remaining solid.

Figure 5:
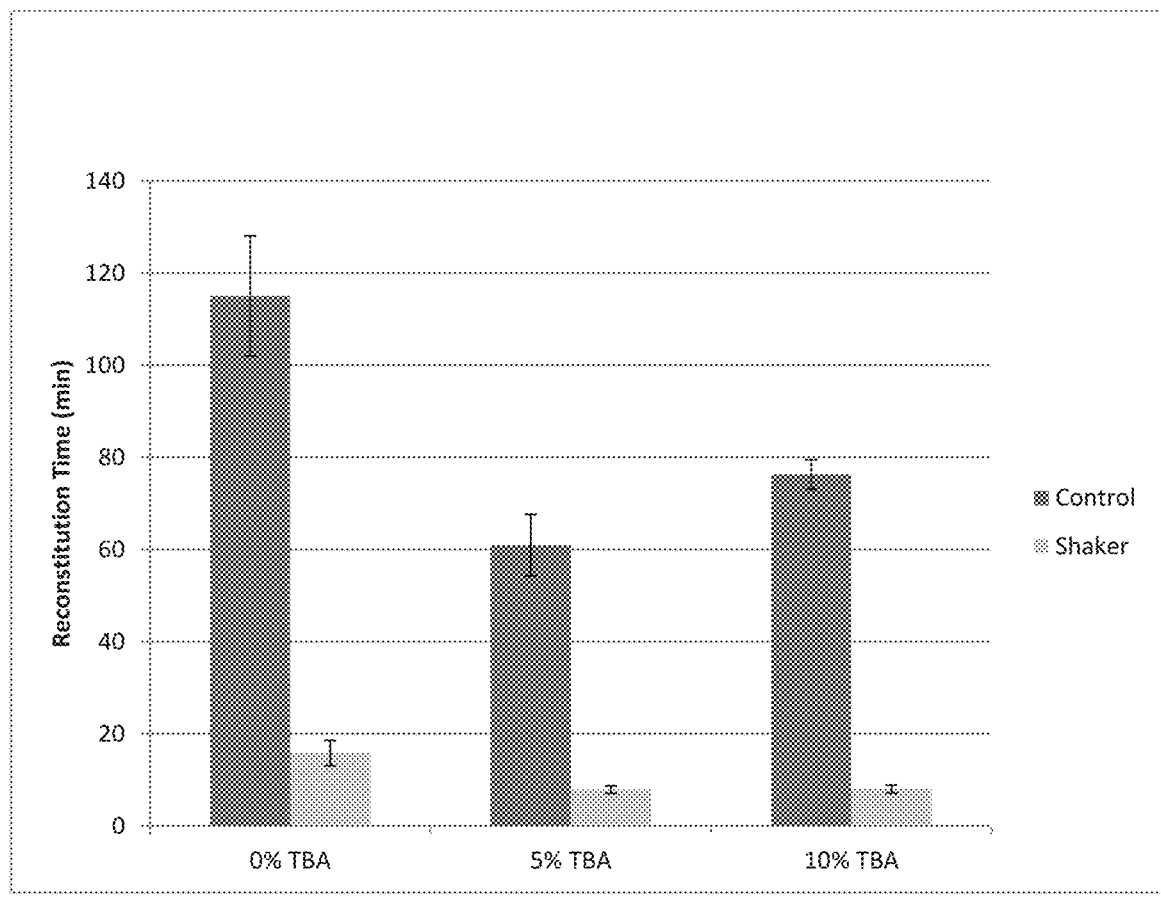
FIG. 5 sets forth data showing the effect of a shaker on reconstitution times for a 100 ml lyophilized antibody formulation containing 0%, 5%, and 10% (v/v) tert-butyl alcohol lyophilized in 100 cc vials.

FIG. 5 shows the effect of different concentrations of TBA (5% and 10% TBA) on reconstitution time of lyophilized mAb1 in 100 cc vials when reconstituted with or without the use of a shaker. As shown in FIG. 5, the addition of either 5% TBA or 10% TBA to the antibody solution prior to lyophilization resulted in a reduction in reconstitution time of mAb1 in the 100 cc vials with 60 ml fill volume. In particular, under control (no shaker) conditions, the addition of TBA prior to lyophilization reduced reconstitution time from greater than 110 minutes with no TBA to approximately 60 minutes with 5% TBA and to approximately 80 minutes with 10% TBA.

When reconstitution was performed using a shaker at 500 rpm, reconstitution times were greatly reduced. In particular, when reconstitution was performed with a shaker, the addition of TBA reduced reconstitution times from approximately 18 minutes with no TBA to approximately 10 minutes with either 5% TBA or 10% TBA.

Taken together, these results showed that combining TBA with shaker showed a greater reduction in reconstitution time compared to using TBA alone.

Example 4. Reconstitution with TBA, Vacuum, and Shaker

The effect on reconstitution time of lyophilized mAb1 when reconstitution was performed under vacuum (100 mTorr) with the aid of a shaker in combination with TBA was examined as follows. For this study, 100 cc vials were used, containing 60 ml fill volume of mAb1 at 70 mg/ml. TBA was added to the mAb1 solutions to a final concentration of either 5% or 10% TBA. Vacuum and shaker conditions were as described above in Example 3.

Figure 6:
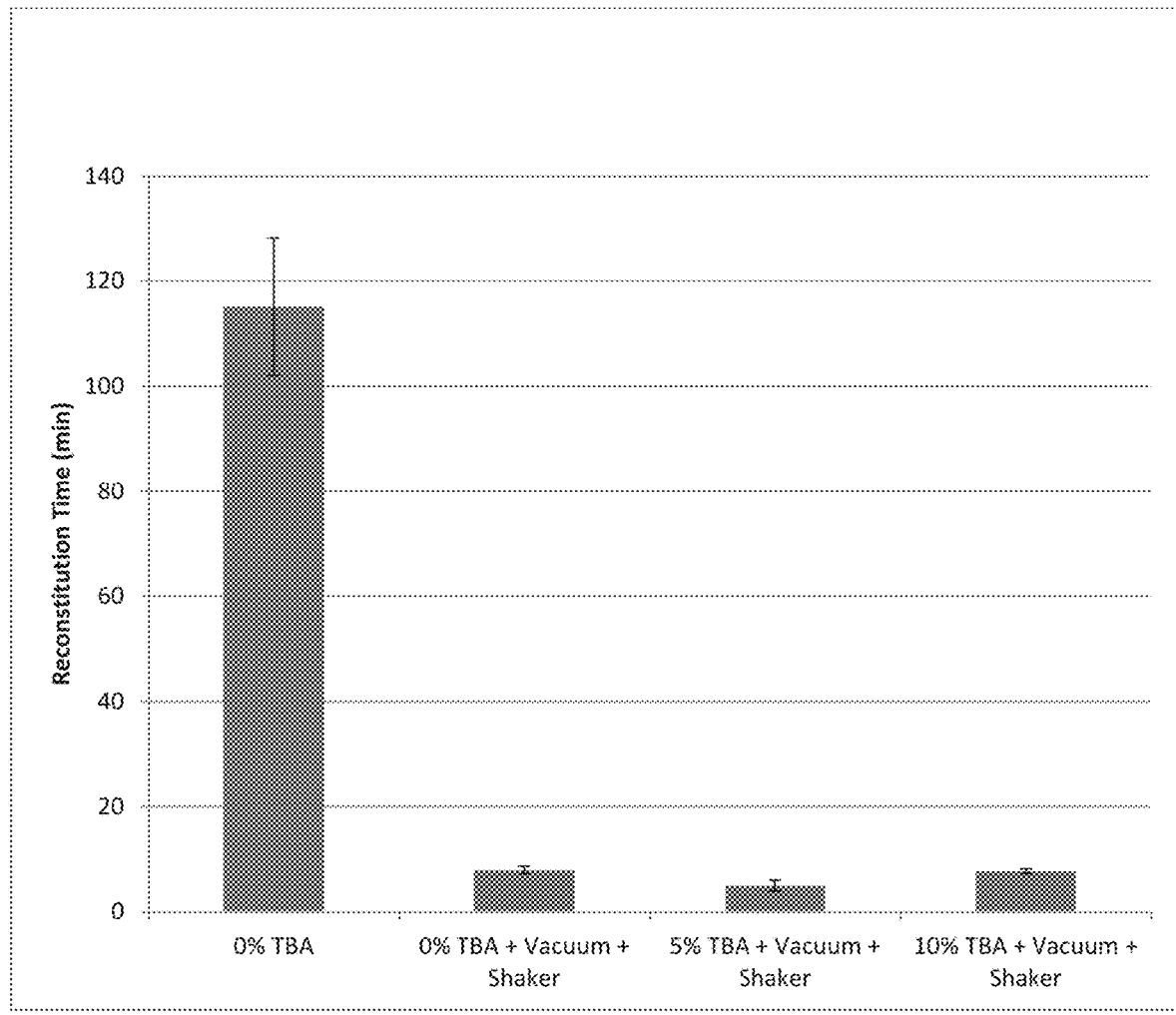
FIG. 6 sets forth data showing the effect of vacuum and a shaker on reconstitution times for a 100 ml lyophilized antibody formulation containing 0%, 5%, and 10% (v/v) tert-butyl alcohol lyophilized in 100 cc vials.

FIG. 6 shows the effect of different concentrations of TBA (5% and 10% TBA) on reconstitution time of lyophilized mAb1 in 100 cc vials when reconstituted under 100 mTorr with the use of a shaker. As shown in FIG. 6, reconstitution took approximately 110 minutes for 100 cc vials containing 60 ml fill with no TBA, no vacuum, and no shaker (swirling for 5 seconds every 10 minutes). However, the addition of vacuum, TBA, and shaker dramatically reduced reconstitution times, to less than 10 minutes; the combination of these three parameters reduced reconstitution time by over 95%.

Using a combination of 5% TBA, vacuum, and shaker, the reconstitution time for 4.2 gm of protein was reduced from an average of 115 minutes to 5 minutes, allowing for the preparation of high-dose biomolecule formulations having rapid reconstitution times.

Figure 7:
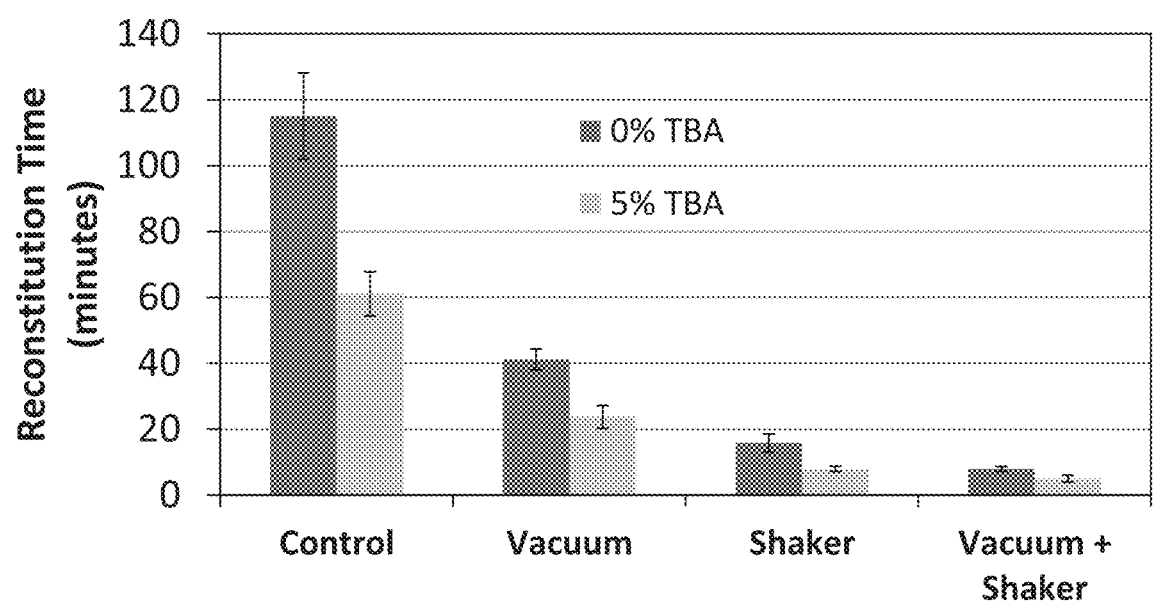
FIG. 7 sets forth data showing the effect of vacuum, shaker, and vacuum and shaker on reconstitution times for a 100 ml lyophilized antibody formulation containing 0% or 5% (v/v) tert-butyl alcohol in 100 cc vials.

FIG. 7 shows the effect of vacuum, shaker, and vacuum and shaker on reconstitution times for a 100 ml lyophilized antibody formulation containing 0% or 5% (v/v) tert-butyl alcohol in 100 cc vials.

Example 5. Liquid Stability Studies

Stability studies to examine the effects of TBA on mAb1 stability in liquid were performed. mAb1 stability was measured by size exclusion chromatography (SEC) and by ion exchange chromatography (IEC). mAb1 (70 mg/ml) was added to 50 cc vials (25 ml fill) containing 0% TBA, 1% TBA, 5% TBA, 10% TBA, or 20% TBA. Vials were then maintained at 2-8° C. or 30° C. for 7 days, during which the stability of the antibody was determined at day 0, day 3, and day 7 for each condition by SEC and IEC analysis.

SEC analysis was performed using an Agilent 1100 or 1200 HPLC (Santa Clara, Calif.) with a Tosoh Biosciences TSK gel 7.8 mm ID×30 cm L column (South San Francisco, Calif.). IEC analysis was performed using an Agilent 1200 HPLC with a Dionex ProPac WCX-10 BioLC™ 4×250 mm Analytical column (Sunnyvale, Calif.).

Figure 8A:
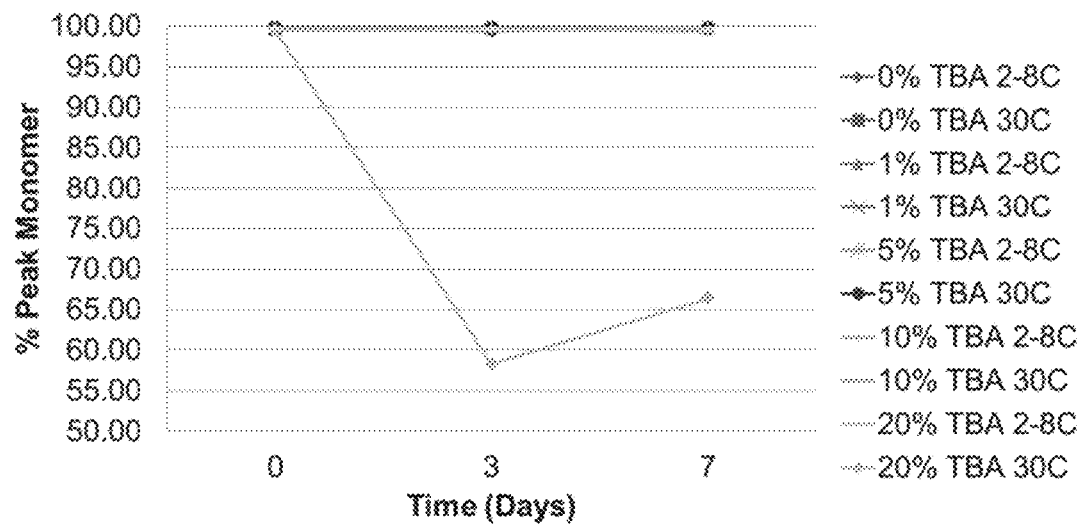
FIGS. 8A and 8B sets forth data showing 7-day stability analysis of an antibody formulation containing 0%, 1%, 5%, 10%, and 20% (v/v) tert-butyl alcohol at either 2-8° C. or 30° C. as measured by size exclusion chromatography (SEC).
Figure 8B:
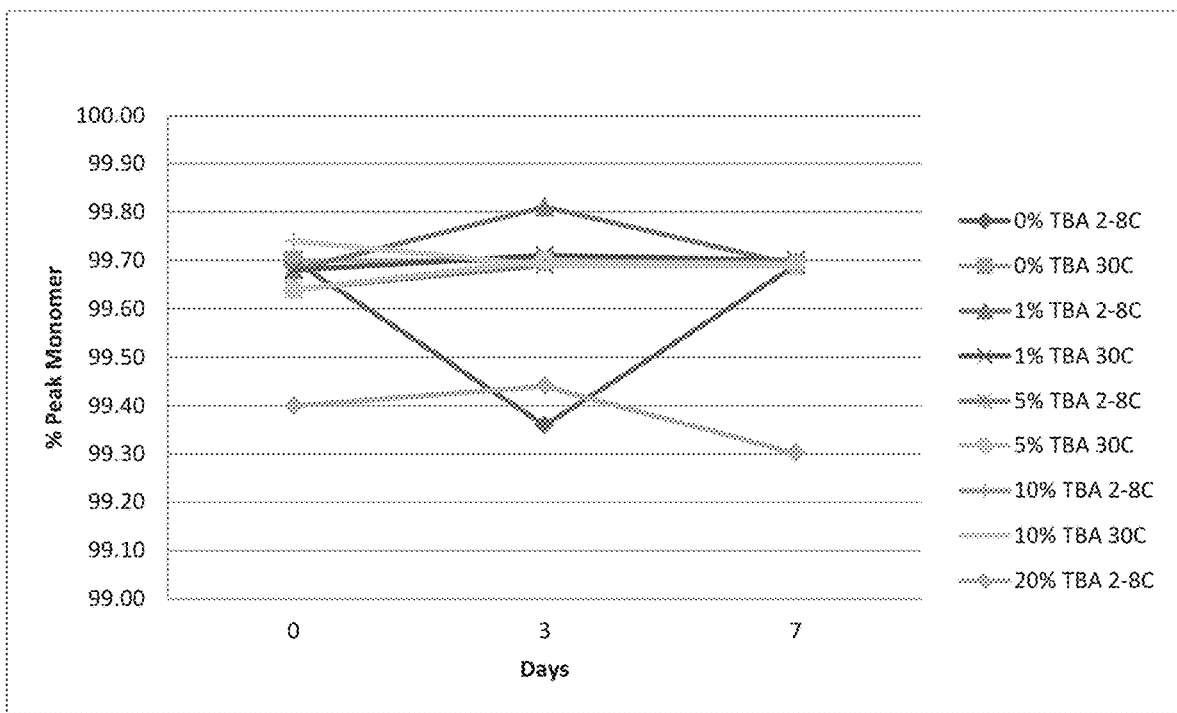

As shown in FIGS. 8A and 8B, mAb1 maintained good stability upon addition of various concentrations of TBA over the course of 7 days at either 2-8° C. or 30° C., as SEC analysis showed maintenance of high percentage of the monomer peak over the course of 7 days. FIG. 8B shows an expanded version of the graph shown in FIG. 8A (that is, FIG. 8B shows the data of FIG. 8A without including the data associated with 20% TBA at 30° C.).

Figure 9:
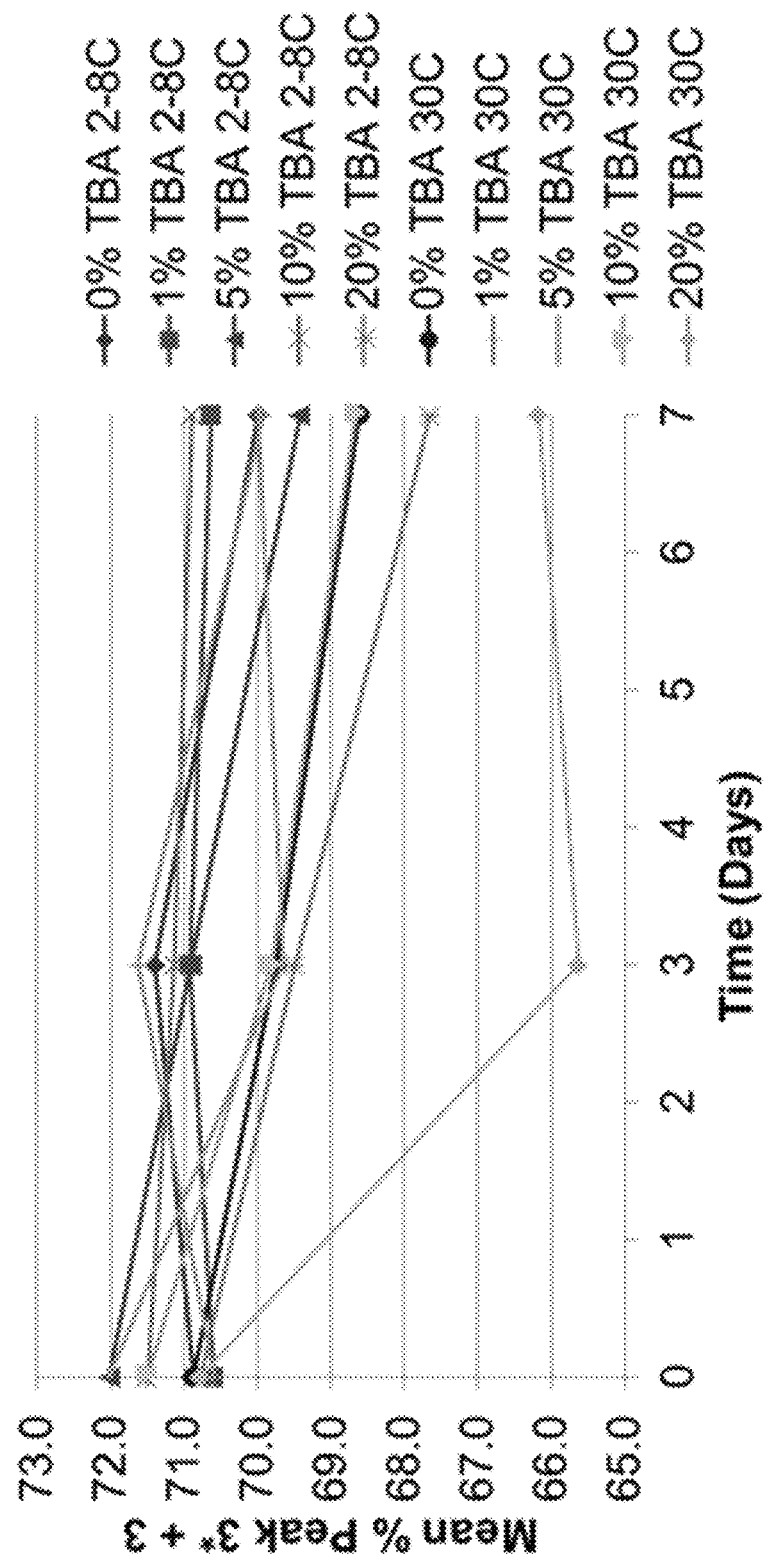
FIG. 9 sets forth data showing 7-day stability analysis of an antibody formulation containing 0%, 1%, 5%, 10%, and 20% (v/v) tert-butyl alcohol at either 2-8° C. or 30° C. as measured by IEC.

As shown in FIG. 9, mAb1 maintained good stability upon addition of various concentrations of TBA over the course of 7 days at either 2-8° C. or 30° C., as IEC analysis showed maintenance of main peak comparable to controls in all cases over the course of 7 days.

Taken together, these results showed that at TBA concentrations below 20% (e.g., 1%, 5%, 10% TBA), stability of the antibody is maintained for at least 7 days; some loss of stability, however, was observed at 20% TBA conditions.

Example 6. Moisture Analysis

The effect of TBA addition to mAb1 or mAb2 prior to lyophilization on the moisture levels of the dried mAbs following lyophilization was examined. mAb1 and mAb2 (both 70 mg/ml) were added to 6 cc vials as described above. TBA was added to the mAb solutions to a final concentration of 0%, 5%, or 10% TBA. The samples were then lyophilized as described above. Following lyophilization, the moisture content of the lyophilized samples (i.e., solid-state samples) was determined using a Mettler Toledo DL31 Volumetric Karl Fischer Titrator (Columbus, Ohio).

As shown in Table 2 below, the addition of TBA does not affect the moisture levels of the lyophilized antibody preparations.

TABLE 2

| Antibody | TBA amount | Moisture (percent) |
| --- | --- | --- |
| mAb1 | 0% TBA | 0.80% |
|  | 5% TBA | 0.81% |
|  | 10% TBA | 0.77% |
| mAb2 | 0% TBA | 0.78% |
|  | 5% TBA | 0.71% |
|  | 10% TBA | 0.78% |

Moisture content was further examined for mAb1 (40 mg/ml in 50 cc vials) with various concentrations of TBA (0%, 5%, 10%) under uncontrolled nucleation (UCN) and controlled nucleation (CN). As shown in Table 3 below, the addition of TBA does not affect the moisture levels of antibody preparations lyophilized using standard freeze technique (uncontrolled nucleation). The addition of TBA decreases the moisture content of antibody preparations lyophilized using controlled nucleation

TABLE 3

| Nucleation condition | TBA amount | Moisture (percent) |
|---|---|---|
| UCN | 0% TBA | 0.67% |
|  | 5% TBA | 0.65% |
|  | 10% TBA | 0.62% |
| CN | 0% TBA | 0.97% |
|  | 5% TBA | 0.44% |
|  | 10% TBA | 0.46% |

The addition of TBA to the monoclonal antibody preparation as shown in both Table 1 and Table 2 show that the addition of TBA does not have much effect on the moisture levels in UCN cakes and decreases moisture levels in CN cakes.

Example 7. BET Analysis to Determine Specific Surface Area

The effect of various concentrations of TBA on specific surface area of the lyophilized antibody cake structure was examined mAb1 and mAb2 were added to 6 cc vials at 70 mg/ml with 0%, 5%, or 10% TBA and lyophilized as described above. Specific surface area measurement was performed with a Quantachrome Quadrasorb Evo Automated Surface Area and Pore Size Analyzer (Boynton Beach, Fla.). Samples were crushed in a glove box with relative humidity<3% and loaded into tared bulbs. A sample size of approximately 100 mg was used. Desorption of residual water was performed at 40° C. with a strong vacuum for at least 3 hours. Multipoint Brunauer-Emmett-Teller (BET) analysis was then performed with relative pressures P/Po of 0.05 to 0.24 using Krypton as the adsorbate.

Table 4 below shows the results of the specific surface area (SSA) determinations, presented as $m^2$/gram. As shown in Table 4 below, the addition of TBA to the antibody preparations prior to lyophilization resulted in an increase in surface area of the lyophilized cakes.

TABLE 4

| Antibody | TBA amount | SA ($m^2$/g) |
|---|---|---|
| mAb1 | 0% TBA | 0.330 |
|  | 5% TBA | 2.262 |
|  | 10% TBA | 6.124 |
| mAb2 | 0% TBA | 0.525 |
|  | 5% TBA | 1.369 |
|  | 10% TBA | 2.835 |

Surface area was further examined using BET analysis for mAb1 (40 mg/ml in 50 cc vials) with various concentrations of TBA (0%, 5%, 10%) with uncontrolled nucleation (UCN) and controlled nucleation (CN). The pore size for the mAb1 cakes with uncontrolled nucleation (UCN) and controlled nucleation (CN) is shown below in Table 5.

TABLE 5

| Nucleation condition | TBA amount | SA ($m^2$/g) |
|---|---|---|
| UCN | 0% TBA | 0.696 |
|  | 5% TBA | 3.668 |
|  | 10% TBA | 2.906 |
| CN | 0% TBA | 0.488 |
|  | 5% TBA | 3.281 |
|  | 10% TBA | 7.794 |

BET analysis suggested that the addition of TBA resulted in differences in pore size and the lyophilized cake structure, possibly due to TBA forming vertical pores as it sublimates during lyophilization. (See Nail, S L et al. Freeze-Drying of tert-Butanol/Water Cosolvent Systems: A Case Report on Formation of a Friable Freeze-Dried Powder of Tobramycin Sulfate. Journal of Pharmaceutical Sciences. Vol. 91, No. 4. April 2002. American Pharmacists Association.)

Example 8. Lyophilized Antibody Stability Studies

Stability studies to examine the effects of TBA in the pre-lyophilization liquid antibody/TBA mixture on the stability of the antibody in the subsequently lyophilized antibody composition were performed. Stability was measured by size exclusion chromatography (SEC).

Figure 10A:
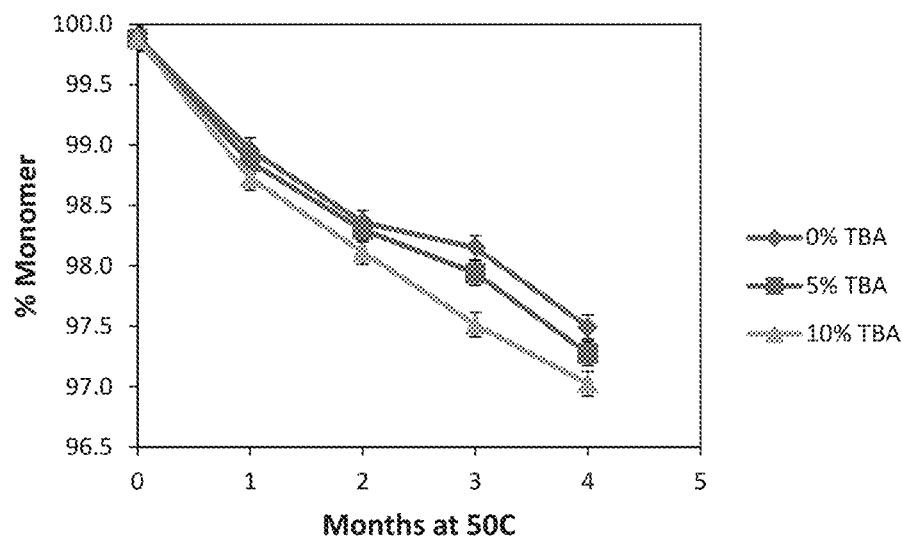
FIGS. 10A and 10B set forth data showing 4-month stability analysis of lyophilized antibody formulations at 50° C. that were generated from pre-lyophilization liquid antibody mixtures containing 0%, 5%, or 10% (v/v) tert-butyl alcohol. Monomer percentages were measured by SEC.
Figure 10B:
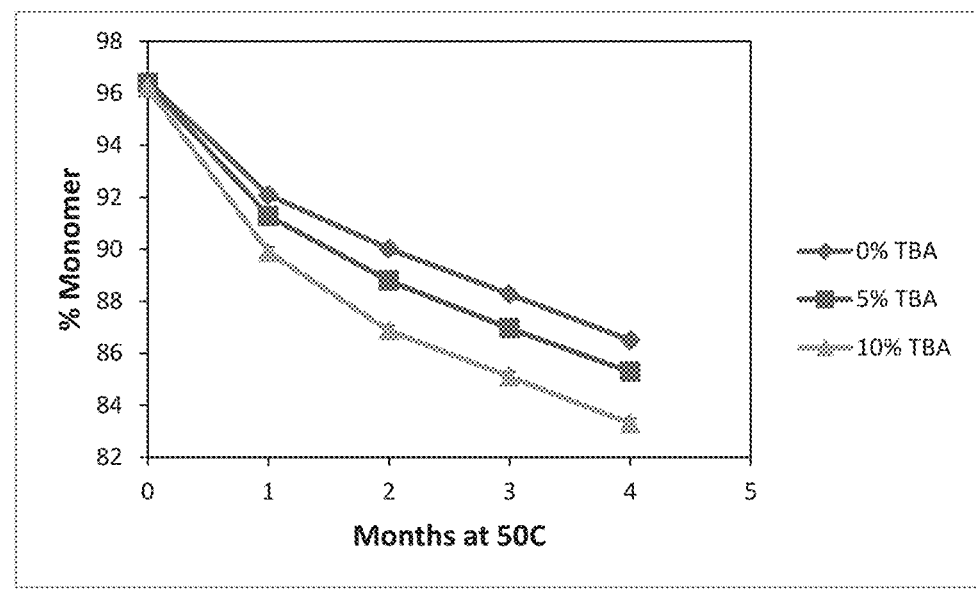

6 cc vials were filled with 2.5 mL of formulations containing 70 mg/mL antibody (mAb1 or mAb2), 168 mM sucrose, 20 mM Histidine HCl at pH 5.8, 0.028% polysorbate 20, and 0, 5, or 10% (v/v) TBA. The vials were lyophilized with a conservative lyophilization cycle and incubated at 50° C. for over four months. Samples were taken monthly and put at −20° C. until batch analysis by size exclusion chromatography. FIG. 10A shows the percentage monomer maintained in the lyophilized mAb1 compositions at each monthly timepoint. FIG. 10B shows the results for the lyophilized mAb2 compositions.

The results show that the accelerated degradation of the lyophilized mAb at 50° C. is still within the typical and acceptable range for lyophilized mAbs when 5% TBA is present in the pre-lyophilization liquid antibody/TBA mixture. As described above, this level of TBA was also shown to minimize the reconstitution time of the lyophilized mAb. Thus, adding 5% TBA to the pre-lyophilization liquid antibody formulation can provide an advantage for high dose lyophilized mAb products that require large (e.g. 50 or 100 cc) vials, and where reconstitution times can be significantly longer compared to smaller volume vials.

What is claimed is:

1. A method for reducing reconstitution time of a lyophilized antibody composition, the method comprising: (a) preparing a liquid composition comprising the antibody and a sugar at a molar ratio of sugar:antibody of at least about 360:1, (b) adding tert-butyl alcohol (TBA) to the liquid composition to form a liquid antibody/TBA mixture, wherein the amount of TBA in the liquid antibody/TBA mixture is about 5%-6% by volume, (c) freezing the liquid antibody/TBA mixture, (d) lyophilizing the frozen antibody/TBA mixture to form a lyophilized antibody composition, (e) reconstituting the lyophilized antibody composition with a diluent, wherein the time for reconstituting the antibody lyophilized in the presence of TBA is less than the time for reconstituting the same amount of the same antibody lyophilized in the absence of TBA.

2. The method of claim 1, wherein the amount of TBA in the liquid antibody/TBA mixture is about 5% by volume.

3. The method of claim 1, wherein the molar ratio of sugar:antibody is between about 360:1 to about 500:1.

4. The method of claim 1, wherein TBA is added to the liquid composition comprising the antibody immediately prior to freezing the liquid antibody/TBA mixture.

5. The method of claim 1, wherein the antibody is a full length antibody.

6. The method of claim 1, wherein the concentration of the antibody in the liquid composition comprising the antibody is between about 10 mg/ml to about 250 mg/ml.

7. The method of claim 1, wherein the amount of the antibody in the liquid composition comprising the antibody is between about 150 mg-11 grams.

8. The method of claim 1, wherein the sugar is sucrose or trehalose.

9. The method of claim 1, wherein the liquid antibody/TBA mixture is lyophilized in a glass vial.

10. The method of claim 9, wherein the glass vial is a 6 cc vial, a 10 cc vial, a 15 cc vial, a 20 cc vial, a 25 cc vial, a 50 cc vial, or a 100 cc vial.

11. The method of claim 9, wherein the glass vial has a fill volume of 2.5 ml, 25 ml, 50 ml, or 100 ml.

12. The method of claim 1, wherein the time for reconstituting the lyophilized antibody composition which was lyophilized in the presence of TBA is reduced by about 40-95% compared to the time for reconstituting the same amount of the same antibody composition lyophilized in the absence of TBA.

13. The method of claim 1, wherein the time for reconstituting the lyophilized antibody composition which was lyophilized in the presence of TBA is reduced by at least about 50% compared to the time for reconstituting the same amount of the same antibody composition lyophilized in the absence of TBA.

14. The method of claim 1, wherein reconstituting the lyophilized antibody composition is performed under conditions in which the lyophilized antibody composition is under a vacuum.

15. The method of claim 14, wherein the vacuum is less than 100 Torr.

16. The method of claim 14, wherein the vacuum is 100 mTorr.

17. The method of claim 1, wherein reconstituting the lyophilized antibody compositing is performed using a shaker.

\* \* \* \* \*